(12) United States Patent
Kwiatkowski et al.

(10) Patent No.: US 6,326,483 B1
(45) Date of Patent: Dec. 4, 2001

(54) COMPOSITIONS AND METHODS BASED UPON THE TUBEROUS SCLEROSIS-1 (TSC1) GENE AND GENE PRODUCT

(75) Inventors: David J. Kwiatkowski, Weston, MA (US); Julian R. Sampson, Cardiff; Margaret S. Povey, Beds, both of (GB); Marjon A. van Slegtenhorst, Hoogland; Dicky J. J. Halley, Rotterdam, both of (NL)

(73) Assignee: Brigham and Women's Hospital, Boston, MA (US)

( * ) Notice: Subject to any disclaimer, the term of this patent is extended or adjusted under 35 U.S.C. 154(b) by 0 days.

(21) Appl. No.: 09/457,708

(22) Filed: Dec. 10, 1999

Related U.S. Application Data

(63) Continuation of application No. PCT/US98/14567, filed on Jul. 15, 1998.
(60) Provisional application No. 60/053,107, filed on Jul. 18, 1997.
(51) Int. Cl.$^7$ .......................... C07H 21/04; C12N 15/00; C12N 1/20; A16K 38/00
(52) U.S. Cl. .................. 536/23.5; 435/320.1; 435/252.3; 530/324
(58) Field of Search ...................... 536/23.5; 435/320.1, 435/252.3; 530/324

(56) References Cited

U.S. PATENT DOCUMENTS 5,532,220    7/1996   Lee et al. .

FOREIGN PATENT DOCUMENTS

WO 95/18226    7/1995   (WO) .

OTHER PUBLICATIONS

Skolnick et al., Trends in Biotechnology, 18(1):34–39, Jan. 2000.*
Killary et al., Methods: A Companion to Methods in Enzymology 8:234–246, 1995.*
Bjornsson, et al., "Tuberous Sclerosis–Associated Renal Cell Carcinoma: Clinical, Pathological, and Genetic Features," *Am. J. Path.* 149(4):1201–1208 (1996).
Buckler, et al., "Exon Amplification: A Strategy to Isolate Mammalian Genes Based on RNA Splicing," *Proc. Natl. Acad. USA* 88:4005–4009 (1991).
Cook, et al., "A Cross Sectional Study of Renal Involvement in Tuberous Sclerosis," *J. Med. Genet.* 33:480–484 (1996).
Ecker, et al., "Measurement of Embryotoxic Factors Is Predictive of Pregnancy Outcome in Women With a History of Recurrent Abortion," *Obstet. Gynecol.* 8184–87 (1993).

European Chromosome 16 Tuberous Sclerosis Consortium, "Identification and Characterization of the Tuberous Sclerosis Gene on Chromosome 16," *Cell* 75:1305–1315 (1993).
Flanagan, et al., "Developmental Enamel Defects in Tuberous Sclerosis: A Clincal Genetic Marker?," *J. Med. Genet.* 34:637–639 (1997).
Fryer, et al, "Evidence that the Gene for Tuberous Sclerosis Is on Chromosome 9," *Lancet* 1(8534):659–661 (1987).
Gomez, "Phenotypes of the Tuberous Sclerosis Complex with a Revision of Diagnostic Criteria," *Ann. N.Y. Acad. Sci.* 615:1–7 (1991).
Green, et al., "Clonality of Tuberous Sclerosis Harmatomas Shown by Non–Random X–Chromosome Inactivation," *Hum. Genet.* 97:240–243 (1996).
Haines, et al., "Localization of One Gene for Tuberous Sclerosis Within $9_q32$—$9_q34$, and Further Evidence for Heterogeneity," *Am. J. Hum. Genet.* 49:764–722 (1991).
Henske, et al. "A High–Resolution Linkage Map of Human $9_q34.1$," *Genomics* 17:587–591 (1993).
Henske, et al., "Identification of VAV2 on $9_q34$ and Its Exclusion as the Tuberous Sclerosis Gene TSC1," *Ann. Hum. Genet.* 59:25–37 (1995).
Henske, et al., "Allelic Loss Is Frequent in Tuberous Sclerosis Kidney Lesions but Rare in Brain Lesions," *Am. J. Hum. Genet.* 59:400–406 (1996).
Hunt et al., "A Prevalence Study of Autism in Tuberous Sclerosis," *J. Autism Develop. Disorders* 23(2):323–339 (1993).
Janssen, et al., "Refined Localization of TSCI by Combined Analysis of $9_q34$ and $16_p13$ Data in 14 Tuberous Sclerosis Families," *Hum. Genet.* 94:437–440 (1994).
Jones, et al., "Molecular Genetic and Phenotypic Analysis Reveals Differences Between TSC1 and TSC2 Associated Familial and Sporadic Tuberous Sclerosis," *Hum. Molec. Genet.* 6(12):2155–2161 (1997), abstract.
Kandt, et al., "Absence of Linkage of ABO Blood Group Locus to Familial Tuberous Sclerosis," *Exper. Neurol.* 104:223–228 (1989).

(List continued on next page.)

Primary Examiner—Christina Y. Chan
Assistant Examiner—Karen Clemens

(57) ABSTRACT

The present invention is directed to a tumor suppressor protein which has been designated hamartin and to the gene, TSC1, which encodes this protein. Mutations in the gene have been found to be associated with certain types of tuberous sclerosis and this has served as a basis for a diagnostic method designed to identify patients that have, or are likely to develop, symptoms associated with this disease. The introduction of the TSC1 gene and subsequent expression of hamartin into cells may be used as a means for treating tuberous sclerosis and other conditions characterized by abnormal cellular growth.

6 Claims, 8 Drawing Sheets

OTHER PUBLICATIONS

Kwiatkowski, et al., "Tuberous Sclerosis," *Arch. Dermatol.* *130*:348–354 (1994).

Maheshwar, et al., "Comparative Analysis and Genomic Structure of the Tuberous Sclerosis 2 (TSC2) Gene in Human and Pufferfish," *Hum. Molec. Genet.* *5*(1):131–137 (1996).

Nagase, et al., "Predication of the Coding Sequences of Unidentified Human Genes. VI. The Coding Sequences of 80 New Genes (KIAA0201–KIAA0280) Deduced of Analysis of cDNA Clones from Cell Line KG–1 and Brain," *DNA Res.* *3*:321–329 (1996).

Nellist, et al., "Identification of Markers Flanking the Tuberous Sclerosis Locus on Chromosome 9 (TSC1)," *J. Med. Genet.* *30*:224–227 (1993).

Povey, et al., "Report on the Third International Workshop on Chromosome 9," *Ann. Hum. Genet.* *58*:177–250 (1994).

Sepp, et al., "Loss of Heterozygosity in Tuberous Sclerosis Hamartomas," *J. Med. Genet.* *33*:962–964 (1996).

Smalley, et al., "Autism and Tuberous Sclerosis," *J. Autism Develop. Disorders* *22*(3):339–355 (1992).

Smith, et al., "BCM Search Launcher—An Integrated Interface to Molecular Biology Data Base Search and Analysis Services Available on the World Wide Web,"*Genome Res.* *6*(5):454–462 (1996).

van Slegtenhorst, et al., "Identification of the Tuberous Sclerosis Gene TSC1 on Chromosome $9_q34$," *Science* *277*:805–808 (1997).

Vrtel, et al., "Identification of a Nonsense Mutation at the 5' End of the TSC2 Gene in a Family with a Presumptive Diagnosis of Tuberous Sclerosis Complex," *J. Med. Genet.* *33*:47–51 (1996).

Wilson, et al., "Novel Mutations Detected in the TSC2 Gene from Both Sporadic and Familial TSC Patients," *Hum. Molec. Genet.* *5*(2):249–256 (1996).

Xu, et al., "Alternative Splicing of the Tuberous Sclerosis 2 (TSC2) Gene in Human and Mouse Tissues," *Genomics* *27*:475–480 (1995).

\* cited by examiner

TGCATGCATGCA

```
GTGCTGTACGTCCAAGATGGGCGGCCCTGTAGGCTGGAGGACTGTGAGGTAAACAGCTGAGGGGAGGAGACGGTGTGACCATGAAAGACACCAGGTT      100
GACAGCACTGGAAACTGAAGTACCAGTTGTGCTAGAACAGTTTGGTAGTGGCCCCAATGAAGACCTTCAGAACCTGTAGCACACGTCCTGGAGCCAGC      200
ACAGGCCCTTGAGCGAGGAGAGAATGGCCCAACAAGCAAATGTGGGGGAGCTTCTTGCCATGCTGGATTCCCCATGCTGGGTGTGCGGGACGAGTGACAG  300
              M   A   Q   Q   A   N   V   G   E   L   L   A   M   L   D   S   P   M   L   G   V   R   D   D   V   T       26
CTGTCTTTAAAGAGAACCTCAATTCTGACGGTGGCCCTATGCTTGTAAACACCTTGGTGGATTATTACCTGGAAACCAGCTCTCAGCCGGCATTGCACAT  400
A   V   F   K   E   N   L   N   S   D   R   G   P   M   L   V   N   T   L   V   D   Y   Y   L   E   T   S   S   Q   P   A   L   H   I    60
CCTGACCACCTTGCAAGAGCCACATGACAAGCACCTCTTGGACAGGATTAACGAATATGTGGGCAAAGCCGCCACTCGTTATCCATCCTCTCGTTACTG   500
L   T   T   L   Q   E   P   H   D   K   H   L   L   D   R   I   N   E   Y   V   G   K   A   A   T   R   L   S   I   L   S   L   L       93
GGTCATGTCATAAGACTGCAGCCATCTTGGAAGCATAAGCTCTCCCAAGCACCTCTTTGCCTTCTTACTAAAATGTCTCAAGATGACACTGACGTCG    600
G   H   V   I   R   L   Q   P   S   W   K   H   K   L   S   Q   A   P   L   L   P   S   L   L   K   C   L   K   M   D   T   D   V      126
TTGTCCTCACAACAGGGTCTTGGTGTTGATAACCATGCTACCCACAGTCTGGGAAACAGCATCTTCTTGATTCTTGACATTTTTGGCCG             700
V   V   L   T   T   G   V   L   V   L   I   T   M   L   P   M   I   P   Q   S   G   K   Q   H   L   L   G   F   F   D   I   F   G   R    160
TCTGTCATCATGGTGCCTGAAGAAACCAGGCCACGTGGGCGGAAGTCTATCTCGTCCATCTCCATGCCAGTGTGTACGCACTCTTCATCGCCTTTATGGA  800
L   S   S   W   C   L   K   K   P   G   H   V   A   E   Y   Y   L   V   H   L   H   A   S   V   Y   A   L   F   H   R   L   Y   G      193
ATGTACCCTTGCAACTTGCGTCTCCTTTTGCGTTCTCATTACAGTATGAAGAAAACTGGAGACTTTGAAGAAGTGGTCAAGCCAATGATGGAGCATG     900
M   Y   P   C   N   F   V   S   F   L   R   S   H   Y   S   M   K   E   N   L   E   T   F   E   E   V   V   K   P   M   M   E   H      226
TGGGAATTCATCGGAATTAGTGACTGGATCCAAGGACCATGAACTGGACCCCTGAAGGTGAAGAGATTAGAAACTCATGATGTGTGATCGAGTGTGC    1000
V   R   I   H   P   E   L   V   T   G   S   K   D   H   E   L   D   P   R   R   W   K   R   L   E   T   H   D   V   V   I   E   C   A   260
```

FIG. 4A

```
CAAAATCTCTCTGGATCCCACAGAAGCCTCATATGAAGATGGCTATTCTGTGTCTCACCAAATATCAGCCCGCTTTCCTCATCGTTCAGCCGATGTCACC  1100
 K  I  S  L  D  P  T  E  A  S  Y  E  D  G  Y  S  V  S  H  Q  I  S  A  R  F  P  H  R  S  A  D  V  T    293
ACCAGCCCTTATGCTGACACAGAATAGCTATGGGTGTGCTACTTCTACCCCTTACTCCAGTCTCGGCTGATGTTGTTAAATATGCCAGGCAGCTAC      1200
 T  S  P  Y  A  D  T  Q  N  S  Y  G  C  A  T  S  T  P  Y  S  T  S  R  L  M  L  L  N  M  P  G  Q  L    326
CTCAGACTCTGAGTTCCCCATCGACAGGCTGATAACTGAACCACCAAGCTACTCTTTGGAGCCCATCTATGGTTTGTGTATGACCACTCCTCCAAC      1300
 P  Q  T  L  S  S  P  S  T  R  L  I  T  E  P  P  Q  A  T  L  W  S  P  S  M  V  C  G  M  T  T  P  P  T  360
TTCTCCTGGAAATGTCCCACCTGATCGTCACACCTTACAGTAAAGTCTTTGGTACAACTGCAGGTGGAAAAGGAACTCCTCTGGAACCCAGCAACC      1400
 S  P  G  N  V  P  P  D  L  S  H  P  Y  S  K  V  F  G  T  T  A  G  G  K  G  T  P  L  G  T  P  A  T    393
TCTCCTCCTCCAGCCCCACTCTGTCATTGGATGACTACGTGGAAATTTCACTCCCCCAGGCCACAGTCACACCCCCAGGAAGGAAGAGAATGGATT      1500
 S  P  P  P  A  P  L  C  H  S  D  D  Y  V  E  I  S  L  P  Q  A  T  V  T  P  P  R  K  E  E  R  M  D    426
CTGCAAGACCATGTCACACAGACAACACCATCTTCTGAATGACAGAGGATCAGAAGAGCCACCTGGCAGCAAAGGTTCGTCACTCTAAGTGATCTTCC    1600
 S  A  R  P  C  L  H  R  Q  H  H  L  L  N  D  R  G  S  E  E  P  P  G  S  K  G  S  V  T  L  S  D  L  P  460
AGGGTTTTAGGTGATCTGGCCTCTGAAGAGGACTCTGAGGAGAAGATAAAGAAGAAGCTGCAATATCTAGAGAACTTTCTGAGATCACCACAGAGAG    1700
 G  F  L  G  D  L  A  S  E  E  D  S  I  E  K  D  K  E  E  A  A  I  S  R  E  L  S  E  I  I  T  A  E    493
GCAGAGCCTGTGGTTCCTCGAGGAGGCTTTGACTCTCCCCTTTACCGAGACAGTCTCCCAGGTTCTCAGCGGAAGACCCACTGGCCAGCCTCCAGTTCTC  1800
 A  E  P  V  V  P  R  G  G  F  D  S  P  F  Y  R  D  S  L  P  G  S  Q  R  K  T  H  S  A  A  S  S  S    526
AGGGGCGCCAGCGTGAACCCTGAGCCTTTACACTCCCTGGACAAGCTTGGGCCTGACACACCAAAGCAAGCCTTTACTCCCATAGACCTGCCCTGCGG    1900
 Q  G  A  S  V  N  P  E  P  L  H  S  S  L  D  K  L  G  P  D  T  P  K  Q  A  F  T  P  I  D  L  P  C  G  560
```

FIG.4B

```
CAGTGCTGATGAAAGCCCTGCGGGAGACAGGGAATGCCAGAGACTTCTTTGGAGACCAGTATCTTCACTCCGACGAGA    2000
 S  A  D  E  S  P  A  G  D  R  E  C  Q  T  S  L  E  T  S  I  F  T  P  S  P        593
GTGGGCTTTGGAAGCGGGCAGCCTCCCCGTATGATCATCTCTTTTGAGGTGGCATTGCCAAAGACAGCCATCATTTTGTCATCAGGAAGACTGAGGAGC    2100
 V  G  F  G  S  G  Q  P  P  P  Y  D  H  L  F  E  V  A  L  P  K  T  A  H  H  F  V  I  R  K  T  E  E    626
TGTTAAAGAAGCAAAAGGAAACACAGAGGAAGATGGTGTGCCCTCTACCTCCCCAATGGAAGTGCTGGACAGGCTGATACAGCAGGGAGCAGACGCGCA    2200
 L  L  K  K  A  K  G  N  T  E  E  D  G  V  P  S  T  S  P  M  E  V  L  D  R  L  I  Q  Q  G  A  D  A  H   660
CAGCAAGGAGCTGAACAAGTTGCCTTTACCCAGCAAGTCTGTGACCTGGACCCACTTGGAGGCTCTCCTTCAGATGAGATCCGCACCCTCCGAGAC    2300
 S  K  E  L  N  K  L  P  L  P  S  K  S  V  D  W  T  H  F  G  G  S  P  P  S  D  E  I  R  T  L  R  D    693
CAGTTGCTTTTACTGCACAACCAGTTACTCTATGAGGTTTTAAGAGGCAGCAGGCGGCTCTCCGCAAGGTGATCAAGCAG    2400
 Q  L  L  L  H  N  Q  L  L  Y  E  R  F  K  R  Q  Q  H  A  L  R  N  R  R  L  L  R  K  V  I  K  A        726
CAGCTCTGGAGGAACATAATGCTGCCATGGAAAGATCAGTTGAAGTTACAAGAGAAGGACATCCAGATGTGGAAGGTTAGTCTGCAGAAAGAACAAGCTAG    2500
 A  L  E  E  H  N  A  A  M  K  D  Q  L  K  L  Q  E  K  D  I  Q  M  W  K  V  S  L  Q  K  E  Q  A  R     760
ATACAATCAGCTCCAGGAGCAGCGTGACACTATGGTAACCAAGCTCCACAGCCAGATCAGAGACGCATGCGACAGGAATTCTACAACCAGAGC    2600
 Y  N  Q  L  Q  E  Q  R  D  T  M  V  T  K  L  H  S  Q  I  R  Q  L  Q  H  D  R  E  E  F  Y  N  Q  S    793
CAGGAATTACAGACGAAGCTGGAGGACTGCAGGAACATGATTGCGGAGCTGCGGATAGAACTGAAGAAGGCCAACAACAAGGTGTCACACTGAGCTGC    2700
 Q  E  L  Q  T  K  L  E  D  C  R  N  M  I  A  E  L  R  I  E  L  K  K  A  N  N  K  V  C  H  T  E  L    826
TGCTCAGTCAGGTTTCCCAAAAGCTCTCAAACAGTGAGTCGGTCCAGCAGCAGCAGATGGAGTTCTTGAACAGGCAGCTGTTGGTTCTTGGGGAGGTCAACGA    2800
 L  L  S  Q  V  S  Q  K  L  S  N  S  E  S  V  Q  Q  M  E  F  L  N  R  Q  L  L  V  L  G  E  V  N  E    860
GCTCTATTTGGAACAACTGCAGAACAAGCACTCAGATACCACAAAGGAAGTAGAAATGAAAGCCGCCTATCGGAAAGAGCTAGAAAAAAACAGAAGC    2900
 L  Y  L  E  Q  L  Q  N  K  H  S  D  T  T  K  E  V  E  M  M  K  A  A  Y  R  K  E  L  E  K  N  R  S    893
```

FIG.4C

```
CATGTTCTCCAGCAGACTCAGAGGCTTGATACCTCTCCCAAAAACGGATTTTGGAACTCACCTGGCCAAGAAAGACCACCTTCTTTTGGAACAGA    3000
 H  V  L  Q  Q  T  Q  R  L  D  T  S  Q  K  R  I  L  E  L  E  S  H  L  A  K  K  D  H  L  L  L  E  Q         926
AGAAATATCTAGAGGATGTCAAACTCCAGGCAAGAGGACAGCTGCAGGCCGCAGAGAGCAGGTATGAGGCTCAGAAAAGGATAACCCAGGTGTTTGAATT    3100
 K  K  Y  L  E  D  V  K  L  Q  A  R  G  Q  L  Q  A  A  E  S  R  Y  E  A  Q  K  R  I  T  Q  V  F  E  L          960
GGAGATCTTAGATTTATATGGCAGGTTGGAGAAAGATGGCCTCTGAAAAAACTTGAAGAAGAAAAGCAGAAGCAGCTGAAGCAGAAGAAAAGGCTT    3200
 E  I  L  D  L  Y  G  R  L  E  K  D  G  L  L  K  K  L  E  E  E  K  A  E  A  A  E  A  A  E  E  R  L          993
GACTGTGTAATGACGGGTGCTCAGATTCCATGGTAGGCACAATGAAGAGGCATCTGGCCACAACGGTGAGACCAAGACCCCAGCCCAGCAGCGCC    3300
 D  C  C  N  D  G  C  S  D  S  M  V  G  H  N  E  E  A  S  G  H  N  G  E  T  K  T  P  R  P  S  S  A        1026
GGGGCAGTAGTGGAAGCAGAGTGGTGGAGGCAGCAGCAGCAGCGAGCTTTCTACCCCAGAGAAACCCCACCACCAGAGGGCAGGCCCATTCAG    3400
 R  G  S  S  G  S  R  G  G  G  G  S  S  S  S  S  S  E  L  S  T  P  E  K  P  P  H  Q  R  A  G  P  F  S     1060
CAGTCGGTGGGAGACGACTATGGGAGAAGCTCTGCCAGCATCCCCACCACTGTGGGCTCACTTCCCAGTTCAAAAAGCTTCCTGGGTATGAAGGCTGA    3500
 S  R  W  E  T  T  M  G  E  A  S  A  S  I  P  T  T  V  G  S  L  P  S  S  K  S  F  L  G  M  K  A  R      1093
GAGTTATTTCGTAATAAGAGCGAGAGCCAGTGTGATGAGGACGGCATGACCAGTAGCCTTTCTGAGAGCTAAAGACAGAACTGGGCAAAGACTGGGTG    3600
 E  L  F  R  N  K  S  E  S  Q  C  D  E  D  G  M  T  S  S  L  S  E  S  L  K  T  E  L  G  K  D  L  G      1126
TGGAAGCCAAGATTCCCTGAACCTAGATGGCCCTCACCCGTCTCCCCCGACCCGGACAGTGTTGGACAGTACATATCATGAGACTCA    3700
 V  E  A  K  I  P  L  N  L  D  G  P  H  P  S  P  P  T  P  D  S  V  G  Q  L  H  I  M  D  Y  N  E  T  H   1160
TCATGAACACAGCTAAGGAATGATGGTCAATCAGTGTTAACTTGCATATTGTGGCACAGAACAGGAGGTGTGAATGCACGTTTCAAAGCTTTCCTGTTT    3800
 H  E  H  S                                                                                              1164
CCAGGGTCTGAGTGCAAGTTCATGTGTGGAAATGGGACGGAAGGTCCTTTGGACAGCTGACTGAATGCAGAACGGTTTTTGGATCTGGCATTGAAATGCCT    3900
```

FIG.4D

COMPOSITIONS AND METHODS BASED UPON THE TUBEROUS SCLEROSIS-1 (TSC1) GENE AND GENE PRODUCT

CROSS REFERENCE TO RELATED APPLICATIONS

The present application is a continuation of PCT/US98/14567 filed on Jul. 15, 1998 and published in English under Article 21(2) of the PCT. The PCT application claims the benefit of U.S. provisional application no. 60/053,107, filed on Jul. 18, 1997.

FIELD OF THE INVENTION

The present invention is directed to the gene TSC1 and to the protein it encodes. TSC1 has the characteristics of a tumor suppressor gene and is often mutated in individuals with a familial form of tuberous sclerosis. The invention also encompasses methods that relate to the gene and gene product.

BACKGROUND OF THE INVENTION

Tuberous sclerosis (TSC) is an autosomal dominant disorder characterized by the development of unusual tumor-like growths (hamartomas) in a variety of organ systems (Gomez, M. R., *Ann. N.Y Acad. Sci.* 615:1–7 (1991); Kwiatkowski, et al., *Arch. Dermatol.* 130:348–354 (1994)). The development of cortical tubers in the brain (regions of abnormal cortical architecture with distinctive large neuronal cells) causes some of the most problematic clinical manifestations of TSC: mental retardation, epilepsy and abnormal behavioral phenotypes including autism and attention deficit-hyperactive disorder (Hunt, et al., *J. Autism. Dev. Disorder* 23:323–339 (1993); Smalley, et al, *J. Autism. Dev. Disorder* 22:339–355 (1992)). Other organ systems commonly involved in TSC include the skin, heart, and kidneys (Kwiatkowski, et al., *Arch. Dermatol.* 130:348–354 (1994)). The lesions seen are often pathognomonic of TSC and include facial angiofibromas, subungual fibromas, forehead plaque, Shagreen patches, cardiac rhabdomyomas and renal angiomyolipomas and cysts. Renal cell carcinoma also occurs at higher frequency and at an earlier age of onset in TSC patients than in normal individuals (Bjornsson, et al., *Am. J. Path.* 149:1201–1208 (1996); Cook, et al., *J. Med. Genet.* 33:480–484 (1996)). About one-third of TSC cases are familial with the remainder being sporadic, i.e., occurring in the absence of a family history of the disease.

Linkage of TSC to 9q34 was first reported in 1987 and this locus was denoted TSC1 (Fryer, et al., *Lancet* i:659–661 (1987)). Subsequent studies provided strong evidence for locus heterogeneity and led to the identification of 16p13 (denoted the TSC2 locus) as a second genomic region showing linkage in some TSC families (Kandt, et al., *Exp. Neurol,* 104:223–228 (1989)). Among families large enough to permit linkage analysis, approximately half show linkage to 9q34 and half to 16p13 (Janssen, et al, *Hum. Genet.* 94:437–440 (1994)).

The TSC2 gene has been isolated and found to consist of 41 coding exons distributed over 45 kb of genomic DNA. It has a message length of 6 kb and encodes several alternatively spliced transcripts and predicted proteins of 1784-1807 amino acids (Maheshwar, et al., *Hum. Mol. Genet.* 5:131–137 (1996); Xu, et al., *Genomics* 27:475–480 (1995)). The occurrence of inactivating germline mutations in TSC2 in patients with tuberous sclerosis and loss of heterozygosity (LOH) at the TSC2 locus in up to 50% of TSC-associated hamartomas support a tumor suppressor function for TSC2 (Carbonara, et al., *Cancer* 15:18–25 (1996); Sepp, et al., *J. Med. Genet.* 33:962–964 (1996)).

Although the TSC2 gene has been isolated and characterized, identification of the TSC1 gene on 9q34 has proven difficult for a number of reasons. Conflicting positional information has been generated by the analysis of meiotic recombination events in TSC families; large genomic rearrangements (e.g., translocations involving this region) have not been discovered; and several parts of the region are unstable in multiple cloning vectors. In addition, the region contains a number of different genes, any one of which could potentially be TSC1. The unambiguous identification of the TSC1 gene would represent a significant advance in several different respects. First, assays designed to identify mutations in TSC1 could be used to help diagnose this condition in patients exhibiting clinical manifestations suggesting that they may suffer from tuberous sclerosis. Similarly, such assays could be used to help identify patients likely to develop the disorder or likely to pass it on to their offspring.

Therapeutically, the identification of the TSC1 gene and its product may provide a tool for the treatment of abnormal cellular growth. In the case of tuberous sclerosis patients, the introduction and expression of the normal TSC1 gene in place of mutated counterparts should help to prevent the development of hemartomas associated with the disease. In addition, the ability to inhibit uncontrolled cellular growth suggests that TSC1 and its product may have therapeutic applications for other conditions characterized by neoplastic growth.

SUMMARY OF THE INVENTION

The present invention is based upon the discovery of a gene (TSC1) which is found within the 9q34 region of chromosome 9. Mutations in TSC1 are associated with familial forms of tuberous sclerosis and the encoded protein, hamartin, has the characteristics of a tumor suppressor.

In its first aspect, the invention is directed to a protein, except as existing in nature, having an amino acid sequence consisting essentially of the sequence shown in FIG. 4 (SEQ ID NO:2). The term "consisting essentially of," is meant to encompass proteins having exactly the same amino acid sequence as shown in the figure, as well as proteins with differences that are not substantial as evidenced by their retaining the basic, qualitative functional properties of hamartin. The phrase "except as existing in nature" encompasses substantially purified forms of the protein as well as forms made by recombinant or synthetic means. A "substantially purified" protein is one that has been separated from other accompanying biological components and will typically comprise at least 85% of a sample, with greater percentages being preferred. Many means are available for assessing the purity of a protein within a sample including analysis by polyacrylamide gel electrophoresis, chromatography and analytical centrifugation.

The invention also encompasses antibodies that bind specifically to hamartin (i.e., that have at least a 100-fold greater affinity for hamartin than any other undenatured protein), and antibodies made by a process involving the injection of a pharmaceutically acceptable preparation of hamartin into an animal capable of antibody production. In a preferred embodiment, monoclonal antibody to hamartin is produced by injecting the pharmaceutically acceptable preparation into a mouse and then fusing mouse spleen cells with myeloma cells.

The invention is also directed to a polynucleotide, except as existing in nature, which encodes a protein consisting essentially of the amino acid sequence of FIG. 4 (SEQ ID NO:2), expression vectors comprising such polynucleotides, and host cells transformed with such vectors. Also included is the human hamartin protein produced by host cells made in this manner. Preferably, the polynucleotide encoding the human hamartin has the sequence shown in FIG. 4 (i.e., that it comprises nucleotides 222–3713 of SEQ ID NO:1). It is also preferred that the vectors and host cells prepared for the expression of hamartin use this particular polynucleotide.

In another aspect, the present invention is directed to a method for identifying a patient that has, or is likely to develop, tuberous sclerosis by determining if the TSC1 gene of the patient is mutated, i.e., by determining whether it contains nucleotide additions, substitutions, or deletions relative to the wild-type TSC1 sequence. The patients examined by this method will typically be those that are exhibiting clinical characteristics suggesting that they may have tuberous sclerosis or individuals that have family members diagnosed as having the disease. In the first case, the method will be used in order to make or confirm a diagnosis and, in the latter case, it will be used to predict whether the patient or their offspring are likely to develop the disease. In general, the likelihood of a patient having or developing tuberous sclerosis increases in proportion to the number and seriousness of TSC1 mutations. Serious mutations include those that cause a frameshift resulting in the misreading of subsequent amino acids or that correspond to specific mutations that have been associated with tuberous sclerosis (see e.g., Table 4).

Any means may be used for determining the extent to which the TSC1 gene has been mutated, including direct nucleotide sequence analysis or hybridization under conditions selected to reveal mutations. However, the preferred method is to amplify one or more regions of the TSC1 gene using the polymerase chain reaction (PCR) and to then analyze the amplification products, e.g., by sequence analysis, heteroduplex analysis, or single strand conformation polymorphism analysis. In a preferred embodiment, the region amplified corresponds to one or more of exons 3–23, with the most preferred exons being 7, 9, 10, 15, 17, 18, 19 and 20.

An analysis of the characteristics of the hamartin protein indicates that it falls within the class of proteins that have been termed "tumor suppressors." Mutations in these proteins which lead to a loss of function are oncogenic and it is recognized that the wild-type forms of the proteins suppress abnormal cellular proliferation. Examples of genes that have been found to encode tumor suppressors include the retinoblastoma susceptibility gene, the p53 gene, and the neurofibromatosis type 1 gene (Weinberg, R. A., *Science* 254:1138–1146 (1991)). Thus, the present invention is directed to a method for treating or preventing the abnormal proliferation of mammalian cells by introducing into the cells DNA encoding hamartin. The DNA must be incorporated into the cells in such a manner that it will undergo expression. In general, this means that the gene must be either operably linked to a promoter that is introduced at the same time as the gene itself or homologous recombination must be used to position the gene downstream from an endogenous promoter. This method may be carried out either on cells in vitro or in vivo. In either case, it is preferred that the cells be selected because they have a mutated form of the TSC-1 gene characteristic of tuberous sclerosis. The most preferred cells for use in conjunction with the method are those containing mutations in exons 3-23, and especially those with mutations in one or more of 7, 9, 10, 15, 17, 18, 19 and 20.

BRIEF DESCRIPTION OF THE FIGURES

FIG. 2A shows a heteroduplex analysis performed on positive samples from the screening population. FIG 2B shows the results of a sequence analysis that reflects a 2105 del AAAG mutation. The sequence reactions were done in antisense orientation, so that reading from the top down b2083–2124 of the normal sequence is shown. The allele sequenced on the left has the deletion, the middle allele is normal, and the sequence on the right is the heteroduplex product with both alleles. FIG. 2C shows the results of an analysis performed in a patient with sporadic TSC. It can be seen that the heteroduplex mobility shift is not present in either parent. FIG. 2D shows the segregation of heteroduplex mobility shifts in a large family with TSC and the digestion of amplification products with MwoI in another family. The results suggest segregation of the 2105delAAAG mutation with the disease.

FIGS. 4A–C: Sequence and Predicted Amino Acid Sequence of the TSC1 Gene. A portion of the nucleotide sequence determined for the TSC1 gene is shown in the figure. The complete sequence, including a 3' untranslated region of approximately 4.5 kb, is shown as SEQ ID NO:1. Nucleotides 222–3713 encode the hamartin structural sequence. The figure also shows the predicted amino acid sequence of hamartin. This has been designated as SEQ ID NO:2. Amino acids 127–144 correspond to a potential transmembrane domain and amino acids 730–965 correspond to a coiled coil domain.

DETAILED DESCRIPTION OF THE INVENTION

Figure 1:
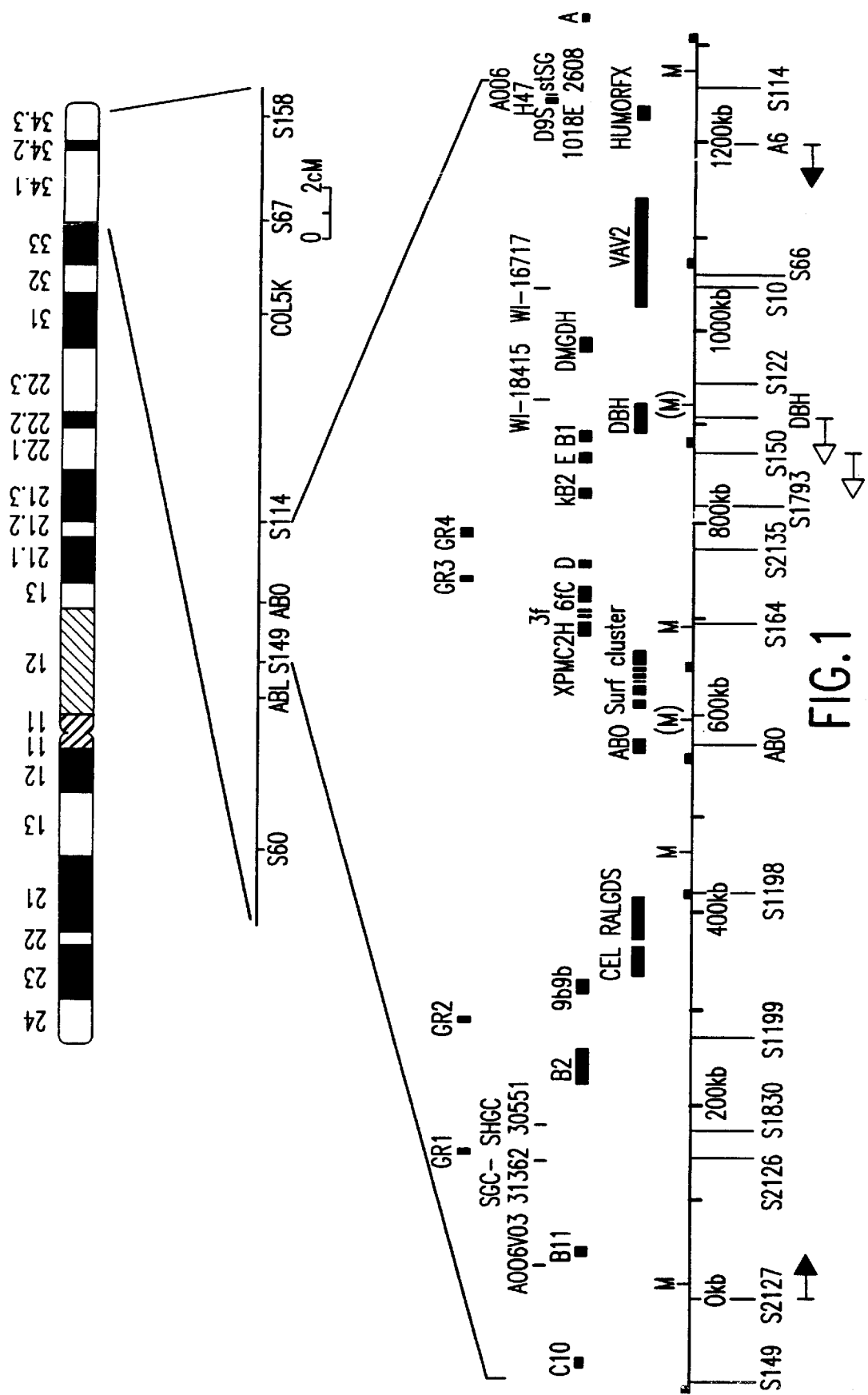
FIG. 1: The TSC1 Region on Chromosome 9: The ideogram (top) represents a normal G-banded metaphase chromosome 9, with the TSC1 region located at 9q34. The male genetic map (middle) shows selected anchor polymorphic loci mapped to 9q34 and the TSC1 candidate region extending from D9S149 to D9S114. The detailed physical map of the candidate region (bottom) shows the positions of polymorphic markers and key recombination events in affected members (filled arrows) and unaffected members (open arrows) of families showing linkage of TSC to 9q34; the approximate positions of MluI sites, M, (with sites which partially cut genomic DNA shown in brackets) and probes used to screen the region for rearrangement in patients with TSC using pulsed field gel electrophoresis; genes previously mapped to the TSC1 candidate region; novel cDNAs isolated from the region; ESTs mapped to the region during this study; and putative genes predicted by GRAIL analysis of genomic sequence. Distances (in kb) from the proximal flanking marker D9S2127 were derived from the sizes of EcoRI fragments in a cosmid contig which spanned the region with one gap of 20 kb near D9S 1793.

The present invention is directed to the hamartin protein, genetic sequences encoding the protein, a method for identifying patients that have or are likely to develop tuberous sclerosis and a method for treating or preventing the abnormal proliferation of mammalian cells. The hamartin protein and the nucleic acids encoding the protein are defined by their structures as shown in FIG. 4.

It will be understood that the present invention encompasses not only sequences identical to those shown in the figures, but also sequences that are essentially the same as evidenced by the protein retaining its basic functional characteristics. For example, it is well known that techniques such as site-directed mutagenesis may be used to introduce variations in a protein's structure. Variations in hamartin introduced by this or by a similar method are encompassed by the invention provided that the resulting protein retains its biological properties, particularly the ability to suppress abnormal cellular growth.

I. Nucleic Acid Sequences Coding for Hamartin

DNA sequences coding for hamartin may be obtained from any tissue or cellular source which expresses the gene. The cells used may either be cultured cells that have not undergone transformation or cell lines specifically engineered to express recombinant hamartin. Many methods are available for isolating DNA sequences and may be adapted for the isolation of hamartin nucleic acid (see, e.g., Sambrook, et al., Molecular Cloning: A Laboratory Manual, 2nd ed., Cold Spring Harbor Press (1989)). One preferred method is to screen a cDNA library that has been prepared by reverse transcribing mRNA isolated from tissues or cells known to express the gene. The library may be prepared from, for example, human fetal brain tissue.

It is expected that a wide variety of probes specific for hamartin can be used equally well for the screening of cDNA libraries. One way to easily produce a large amount of probe is to use the polymerase change reaction (PCR) to amplify the desired sequence from a cDNA library. A listing of primers that have been found to be suitable for amplfying specific exons of the hamartin gene is shown in Table 3.

Amplified fragments can be size fractionated on an agarose gel and the selected fragments (based upon the expected size of the exon amplified) inserted into an appropriate vector and introduced into competent cells by any of the established methods for cell transformation, e.g. by calcium phosphate precipitation. Transformed cells containing the DNA of interest may be identified either by hybridization with a radiolabeled probe specific for the exon in question or by PCR amplification using primers complementary to a region of the exon. The DNA inserts present in the cells are excised, purified and labeled with $^{32}P$. The labeled DNA fragments thus produced are used as probes for screening a cDNA library for hamartin. The presence of the correct sequence in selected cells may be confirmed by DNA sequencing and, if necessary, partial clones may be spliced together to form a full length sequence.

Although the above procedure is suitable for obtaining hamartin nucleic acid, it is expected that alternative techniques can be developed with relatively little effort. Thus, cDNA libraries may be screened using probes synthesized based upon the sequence shown in FIG. 4. In general, the probes should be at least 14 nucleotides long and should not be selected from a region known to be conserved among proteins. Alternatively, using the sequences shown in the figure, it should be possible to select PCR primers and amplify the full length hamartin sequence.

II. Production and Isolation of Hamartin Recombinant Protein

In order to express recombinant hamartin, the DNA encoding the structural sequence of the protein must be placed in a vector containing trascriptional and translational signals recognizable by an appropriate host. The cloned hamartin sequences, preferably in double stranded form, are inserted into the expression vector in an operable linkage, i.e., they are positioned so as to be under the control of regulatory sequences found in the vector and in such a manner that mRNA is produced which is translated into the harnartin amino acid sequence.

Expression of the hamartin protein in different hosts may result in different post-translational modifications that can, potentially, alter the properties of the protein. Preferably, nucleic acid encoding hamartin is expressed in eukaryotic cells, especially mammalian cells. These cells provide post-translational modifications which, inter alia, aid in the correct folding of the protein. Mammalian cells that may be used include, without limitation, NIH-3T3 cells, CHO cells, HeLA cells, LM(tk-) cells, etc. Vectors suitable for each of these various cell types are well known in the art (see e.g. Sambrook, et al, supra). Preferred eukaryotic promoters include that of the mouse metallothionein I gene, the TK promoter of Herpes virus; the SV40 early promoter; and the CMV early promoter. Some examples of suitable prokaryotic promoters include those capable of recognizing T4 polymerases, the $P_R$ and $P_L$ promoters of bacteriophage lambda, and the trp, recA, heat shock and lacZ promoters of E coli.

Expression vectors may be introduced into host cells by methods such as calcium phosphate precipitation, microinjection, electroporation or viral transfer. Cells expressing hamartin can be selected using methods well known in the art. One simple method for confirming the presence of the hamartin nucleic acid in cells is to perform PCR amplification using the procedures and primers discussed above.

Recombinant hamartin protein may be purified using standard techniques well known in the art. These may include filtration, precipitation, chromatography and electrophoretic methods. Purity can be assessed by performing electrophoresis on a polyacrylamide gel and visualizing proteins using standard staining techniques.

III. Antibodies to Hamartin

The present invention is also directed to antibodies that bind specifically to hamartin and to a process for producing such antibodies. Antibodies that "bind specifically to hamartin" are defined as those that have at least a 100 fold greater affinity for hamartin than for any other undenatured protein. The process for producing such antibodies may involve either injecting the hamartin protein itself into an appropriate animal or, preferably, injecting short peptides made to correspond to different regions of hamartin. The peptides should be at least 5 amino acids in length and should be selected from regions believed to be unique to the protein. Thus, highly conserved regions should generally be avoided in selecting peptides for the generation of antibodies. Methods for making and detecting antibodies are well known to. those of skill in the art as evidenced by standard reference works such as: Harlow, et al., Antibodies, A Laboratory Manual, Cold Spring Harvar Laboratory, M.Y. (1988); Klein, Immunology: The Science of Self-Nonself Discrimination (1982); Kennett, et al., Monoclonal Antibodies and Hybridomas: A New Dimension in Biological Analyses (1980); and Campbell, "Monoclonal Antibody Technology," in Laboratory Techniques in Biochemistry and Molecular Biology (1984).

"Antibody," as used herein, is meant to include intact molecules as well as fragments which retain their ability to bind to antigen (e.g., Fab and $F(ab')_2$ fragments). These fragments are typically produced by proteolytically cleaving intact antibodies using enzymes such as papain (to produce Fab fragments) or pepsin (to produce $F(ab')_2$ fragments).

The term "antibody" also refers to both monoclonal antibodies and polyclonal antibodies. Polyclonal antibodies are derived from the sera of animals immunized with the antigen. Monoclonal antibodies can be prepared using hybridoma technology (Kohler, et al., *Nature* 256:495 (1975); Hammerling, et al., in: Monoclonal Antibodies and T-Cell Hybridomas, Elsevier, N.Y., pp. 563–681 (1981)). In general, this technology involves immunizing an animal, usually a mouse, with either intact hamartin or a fragment derived from hamartin. The splenocytes of the immunized animals are extracted and fused with suitable myeloma cells, e.g., $SP_2O$ cells. After fusion, the resulting hybridoma cells are selectively maintained in HAT medium and then cloned by limiting dilution (Wands, et al., *Gastroenterology* 80:225–232 (1981)). The cells obtained through such selection are then assayed to identify clones which secrete antibodies capable of binding to hamartin.

The antibodies or fragments of antibodies of the present invention may be used to detect the presence of hamartin protein in any of a variety of amino assays. For example, antibodies may be used in radioimmunoassays or in immunometric assays, also known as "two-site" or "sandwich" assays (see Chard, T., "An Introduction to Radioimmune Assay and Related Techniques," in: Laboratory Techniques in Biochemistry and Molecular Biology, North Holland Publishing Co., N.Y. (1978)). In a typical immunometric assay, a quantity of unlabeled antibody is bound to a solid support that is insoluble in the fluid being tested, e.g. blood, lymph, cellular extracts, etc. After the initial binding of antigen to immobilized antibody, a quantity of detectably labeled second antibody (which may or may not be the same as the first) is added to permit detection and/or quantitation of bound antigen (see e.g. Radioimmune Assay Method, Kirkham et al., ed., pp. 199–206, E&S Livingstone, Edinburgh (1970)). Many variations of these types of assays are known in the art and may be employed for the detection of hamartin.

Antibodies may also be developed that are specific for mutated exons of hamartin that have been shown to be associated with TSC. A list of specific mutations for exons 7, 9, 10, 15, 17, 18, 19 and 20 may be found in Table 4. One or more of these mutations may be introduced into the TSC1 DNA by a variety of techniques. The appropriate exon may then be amplified, cloned into an appropriate expression vector and recombinantly produced. Monoclonal antibodies may be generated by the techniques discussed above and those specific for mutated forms of hamartin selected by comparing their ability to bind to the mutated exon and its wild-type counterpart.

Antibodies to hamartin may also be used in the purification of either the intact protein or fragments of the protein (see generally, Dean et al., Affinity Chromatography, A Practical Approach, IRL Press (1986)). Typically, antibody is immobilized on a chromatographic matrix such as Sepharose 4B. The matrix is then packed into a column and the preparation containing hamartin is passed through under conditions that promote binding, e.g. under conditions of low salt. The column is then washed and bound hamartin is eluted using a buffer that promotes dissociation from antibody, e.g. buffer having an altered pH or salt concentration. The eluted hamartin may be transferred into a buffer of choice, e.g. by dialysis, and either stored or used directly.

IV. Assays for Patients that Have or are Likely to Develop Tuberous Sclerosis

Although there are clinical criteria for determining whether a patient has tuberous sclerosis, a diagnosis may be difficult to make in cases where symptoms are marginal or the onset of the disease is protracted. The present invention provides a diagnostic method for confirming that a patient has tuberous sclerosis and for identifying individuals that carry forms of the TSC1 gene that are likely to lead to the onset of the disease either in themselves or their offspring.

The basic concept that reduced or aberrant expression of the TSC1 gene is associated with tuberous sclerosis has been established by the experiments discussed below in the Examples section. This concept is the basis of the present diagnostic method which has as its essential feature the determination of whether mutations exist in the TSC1 nucleotide sequence or whether the gene is under-expressed. Table 4 lists a series of mutations that have been found to be specifically associated with patients having TSC. An indication that one or more of these mutations are present would be a strong indication that the patient examined, or their offspring, are likely to develop TSC-associated symptoms.

Other mutations would also be indicative of a propensity to the disease with the likelihood of disease development or presence correlating directly with the seriousness of the mutations in terms of disrupting the biological function of the gene product. For example, deletions, rearrangements or additions that resulted in a substantial misreading of the hamartin amino acid sequence would be a very strong positive result. The same is true with regard to the expression of the gene. Thus, patients who expressed substantially less (e.g., 50% or less) of the hamartin protein relative to control individuals known not to have TSC or come from a family in which the disease is present, would stand a strong likelihood of developing TSC-associated symptoms even if they had a normal TSC1 genotype.

Methods for analyzing mutations within the TSC2 gene have been established (WO 95/18226; Vrtel, et al., *J. Med. Genet.* 33:47–51 (1996); Wilson et al., *Hum. Mol. Genet.* 5:249–256 (1996)) and, with minor modifications, these can be readily adapted to the analysis of mutations in TSC1. Thus, a preferred way to carry out the analysis involves using PCR to amplify either the entire TSC1 gene or segments of the gene and then analyzing the amplification products for mutations by single strand conformation polymorphism analysis, heteroduplex analysis, or by direct sequencing of amplified DNA. Methods and primers that have proven successful for the amplification of different regions of TSC1 are described in the Examples section.

For example, exons 9–23 of TSC1 may be amplified using the primers shown in Table 3. The complimentary strands of the amplified exons are then denatured and the individual strands are diluted to allow each molecule to assume a secondary structural conformation. These strands are then subjected to electrophoresis under non-denaturing conditions and the electrophoretic pattern obtained for the sample is compared to the pattern obtained using a control sample obtained from an individual having a normal TSC1 genotype. Any amplification product showing an electrophoretic pattern different from the pattern obtained from the control can then be sequenced to determine the exact mutations present. Additional assays may be performed to determine the amount of hamartin expressed in the cells of a patient, e.g., in cells from biopsy tissue. Assays based upon antibodies such as those described above may be adapted for this purpose.

Although a finding that the TSC1 gene is either under-expressed or mutated suggests that a patient will develop TSC, a finding of normal expression would not necessarily lead to the conclusion that the patient either does not have the disease or will not develop it. Only about half of the patients with a familial form of TSC show linkage indicating an aberration with respect to TSC1 expression. The other half appear to have abnormalities associated with the TSC2 gene. Therefore, it is expected that the present assay will find its greatest effectiveness when combined with assays for TSC2 (see, e.g., WO 95/18226) and used on patients selected for testing either because they have symptoms suggestive of TSC or who come from a family where the disease has been prevalent.

V. Method of Treating or Preventing Abnormal Cellular Proliferation Using TSC1

The characteristics of the TSC1 gene product, i.e., hamartin, indicate that it falls into the category of proteins termed "tumor suppressors." Mutations resulting in a loss of function of these proteins are associated with tumor formation, and in the case of TSC1, are associated with the development of hamartomas in the brain and other organs. As with other tumor suppressors (see e.g., U.S. Pat. No. 5,532,220), the introduction into cells of DNA expressing the wild-type TSC1 sequence provides a means for inhibiting abnormal, uncontrolled cellular growth. The preferred method for accomplishing this is by operably linking DNA encoding hamartin to a promoter that is active in eukaryotic cells, e.g., the CMV early promoter, and introducing this construct into cells by means of a recombinant retrovirus, e.g., a retrovirus derived from Maloney murine leukemia virus. Standard techniques for the production of appropriate retroviral vectors have been described in the art (see e.g., U.S. Pat. No. 5,532,220).

Although the introduction of DNA encoding hamartin is most clearly relevant to the treatment of patients with TSC caused by mutations in TSC1, it is expected that the present techniques will have application in the control of abnormal cellular growth in other patients as well. Thus, the method may find application in the treatment of patients with a tendency to form polyps, or who have a variety of neoplasms.

VI. Uses of the Present Invention

The utility of certain aspects of the present invention should be readily apparent from the discussion above. Methods for diagnosing TSC and counseling individuals that come from families where the disease is prevalent is of clear value in clinical medicine. The TSC1 gene can be used to provide fragments, controls, and primers for use in such assays and has independent value in ascertaining the levels at which TSC1 is being expressed in patients and in the treatment of abnormal cellular growth.

In addition to diagnostic and therapeutic methods based upon the TSC1 gene and mutated forms of the gene, such methods may also be based upon the gene product, i.e,. the hamartin protein. For example, the protein may be directly assayed to determine whether its levels are indicative of a normal individual or one likely to develop symptoms characteristic of TSC. Such analyses can probably best be performed using antibody-based assays such as those described above in section III. Thus, the hamartin protein can be used to generate antibodies useful in diagnostic assays. Beyond this, monoclonal antibodies binding only to forms of hamartin containing mutations associated with TSC1, may form the basis of alternative diagnostic procedures. The hamartin protein may be used in the development of appropriate antibodies as well as a control in such assays.

EXAMPLES

I. Methods

Patients

Patients used in the present study were diagnosed as having tuberous sclerosis according to standard diagnostic criteria (Kwiatkowski, et al., *Arch Dermatol.* 130:348–354 (1994); Roache, et al., *J. Child Neruol.* 7:221–224 (1992)). Blood samples were obtained after informed consent (approved by local human research committee), and used either directly or after the creation of immortalized Epstein-Barr virus transformed lymphoblastoid cell lines, for the preparation of DNA by standard methods. Families were considered to demonstrate linkage to the TSC1 region if they: 1) demonstrated obligate recombination with markers within 2 cM of the TSC2 gene; and 2) had positive lod scores after analysis with DNA markers from the chromosome 9q34 region (see FIG. 1). Each of the three families used to identify critical recombination events have been previously described (Haines, et al. *Am. J. Hum. Genet.* 49:764–772 (1991); Nellist, et al., *J. Med. Genet.* 30:224–227 (1993); Au, et al., *Am. J. Path.* 149:1201–1208 (1996)). Families providing critical recombinant events were analyzed using multiple markers from the 9q34 region, and haplotype analysis was performed manually to identify the site of recombination.

Gene Identification and Other Methods

Exon trapping was performed according to standard methods and as described previously (Buckler, et al., *Proc. Nat'l Acad. Sci.* USA 88:4005–4009 (1991); Henske, et al., *Am. J. Hum. Genet.* 59:400–406 (1996)). Briefly, cosmid, BAC or PAC was digested with PstI or BamHI, and a library of subclones prepared in the pSPL3 vector. This library was then electroporated into cos cells, RNA was collected two days later, RT-PCR performed, a library of exon fragments prepared in the plasmid pGEMblue, and selected clones sequenced. Exons identified in this manner were used to: 1) screen cDNA libraries by conventional methods; 2) screen Genbank and dbEST databases; and 3) used in RT-PCR experiments, all to identify cDNA clones. Image clones were obtained from Research Genetics or the UK HGMP Resource Centre.

cDNA selection was performed using the end ligation coincident sequence cloning method as described by Brookes, et al., *Hum. Mol. Genet.* 3:2011–2017 (1994). A normalized infant brain cDNA library (Soares, et al., *Proc. Nat'l Acad. Sci.* USA 91:9228–9232 (1994)) was screened using whole cosmids as probes by standard methods. A human fetal brain cDNA library (Clontech) was screened by standard phage plating and filter lift methods.

5' RACE was performed using the Marathon cDNA kit (Clontech), with oligonucleotides derived from B2 cDNA clones, or inferred by analysis of genomic sequence information using the GRAIL program (Xu, et al., *Genomics* 27:475–480 (1995)). RACE and other cDNA clones were sequenced fully on both strands using Taq cycle sequencing methodology and labeling with $^{32}P$ followed by autoradiography, or using an ABI automated sequencer according to standard protocols.

Pulsed field gel electrophoresis was performed to analyze large DNA fragments as described previously (Consortium, *Cell* 75:1305–1315 (1993)). MluI digestion of DNA embedded in agarose plugs was followed by electrophoresis in a CHEF DRII apparatus and then transferred to nylon filters. Southern blotting for analysis of smaller DNA fragments (1–20 kb) was performed according to standard methods. Probes were labeled with $^{32}P$ by random priming in the presence of $^{32}PdGTP$, and hybridization and rinsing were performed at 65° C. in 0.6 M and 60 mM NaCl buffers respectively.

Northern blot analysis was performed by conventional methods using multiple tissue Northern blots (Clontech).

Hybrid Methods

A panel of hybrid cell lines was established to permit analysis of the TSC1 mutation-bearing chromosome 9. 15

TSC families with lod scores greater than 1, with TSC1 region markers and negative linkage with TSC2 region markers were selected for these experiments. The Chinese hamster ovary cell line CHO-K1, which is GAT-, i.e., requires glycine, adenine and thymidine for growth (Kao, et al., *Proc. Nat'l Acad. Sci USA* 60:1275–1281 (1968)) was fused to lymphoblastoid cell lines derived from TSC patients and hybrids retaining chromosome 9 were selected in growth medium lacking glycine (Fournier, et al. Somat. *Cell Genet.* 9:69–84 (1983)). Hybrids with retention of chromosome 9 bearing the affected TSC1 allele were identified by analysis with TSC1 region markers (FIG. 1) and used for analysis by PCR.

Genomic Sequencing and Data Management

Approximately 36 cosmids covering 1.2 Mb on 9q34 were chosen to represent a minimal tiling path across the region based upon EcoRI restriction fingerprints (Horniglov, et al., *Genomics* 41:385–389 (1997)). Cosmid DNA was sheared using a Fisher Scientific 550 Dismemberator Sonicator, and repaired using Mung Bean nuclease (New England Biolabs, Beverly, Mass.), size selected by 2 rounds of agarose gel electrophoresis, and fragments from 1.5–2.5 kb were excised and ligated into SmaI cut M13mp18. After transformation into XL2Blue and plating, single clear plaques were picked using an automated picking device (PBA Technologies, Cambridge, UK), expanded with JM101, and phage supernatant collected. M13 DNA isolation was performed using the Sequatron Robotic system (Hawkins, et al., *Science*, in press (1997)) following the solid-phase reversible immobilization protocol (Hawkins, et al., *Nucl. Acids Res.* 22:4543–4544 (1994)). Dye primer DNA sequencing used energy transfer (ET) primers and thermosequenase (Amersham, Chicago, Ill.). After thermal cycling, the reactions were pooled and precipitated with ethanol, resuspended, heated and loaded onto an Applied Biosystems 377 DNA Sequencer.

Once approximately tenfold coverage was attained per cosmid (typically 1200 reads) the gel files were extracted, signal processed and basecalled using Trout (a UNIX based gel analysis package available at ftp from genome.wi.mit.edu/distribution/software/trout) and then assembled using Alewife, a sequence assembly package. Typically, the sequencing reads from a single cosmid assembled into 1–3 contigs, which were then finished by directed primer walking, and directed selection of reverse reads from existing M13 templates to span sequence gaps. Finally, completed projects were analyzed for common repeats entomologies to existing database entries and submitted to GenBank.

Analysis of Genomic Sequence and Mutation Analysis

Genomic sequence was analyzed using the program GRAIL2 to identify possible exons and gene models. Putative transcriptional units were also identified by BLAST searches of public databases and comparison with our own collection of cDNA clones and exon trapping products. These were confirmed by RT-PCR experiments in most cases. Known or putative exons identified by these techniques were analyzed for mutations.

A screening set of 60 DNA samples, 20 from patients from families with linkage to 9q34 and 40 from sporadic patients, was used. Oligonucleotide primers were designed to be external to exons by 40–60 bp, and following application on the screening set, DNAs were analyzed for heteroduplex formation using weak denaturing gels (Couch, et al., *Nat. Genet.* 13:123–126 (1996); Ganguly, et al., *Proc. Nat'l Acad. Sci USA* 90:10325–10329 (1993)). Briefly, following amplification, PCR products were heated to 95° C. for 5 minutes, and then incubated at 65° C. for 1 hour. Samples were mixed with 30% formamide and 20% ethylene glycol and immediately loaded on large (35×45 cm) 6% polyacrylamide gels (29:1 acrylamide:bis), containing 15% formamide and 10% ethylene glycol, using an 89 mM tris, 15 mM taurine, 0.5 mM EDTA gradient buffer. After electrophoresis for 2–6 hours, gels were stained with 1 mg/ml ethidium bromide for 5 minutes, rinsed with water, and visualized with 300 nm UV light. Similar techniques were also used for smaller (20 cm×30 cm) gels in some cases. DNA products with mobility shifts were subjected to sequence analysis of both strands, as described above. Some products were subcloned into plasmid vectors to facilitate analysis of individual alleles.

Single strand conformation polymorphism (SSCP) gels were also used to search for mutations, after the initial screening. These were generally run in 1X TBE, using 10% acrylamide gels (37.5:1 acrylamide:bis), under two conditions for 16 cm gels: 20° C. at 400 V for 4 hours, and 4° C. at 100 V for 16 hours. Pre-digestion with Sau3A and/or HinfI was used for longer PCR products in some cases. DNA fragments were visualized by silver staining or through use of $^{32}P$ to label PCR products and autoradiography. PCR products with abnormally migrating bands were subjected to sequence analysis.

II. Results

Defining the TSC1 Critical Region

FIG. 1 illustrates the consensus critical region to which TSC1 has been localized (Au, et al., *Am. J. Path.* 149:1201–1208 (1996); Povey, et al., *Ann. Hum. Genet.* pp. 9–11 (April, 1994)). The limiting centromeric and telomeric markers are based upon analysis of affected individuals (solid arrows at bottom) from families with individual lod scores of 2 and 4, respectively. These limits are also consistent with LOH studies which have shown the occurrence of LOH for 9q34 markers in 10 of 158 hamartomas from TSC patients, with identification of D9S149 as the proximal limit of LOH in 3 lesions, and D9S298 as the distal limit in 2 lesions (Henske, et al., *Ann. Hum. Genet.* (1995); Sepp, et al., *J. Med. Genet.* 33:962–964 (1996)). Also shown in FIG. 1 are two additional recombination events occurring in unaffected individuals (open arrows), also from families with lod scores of 2 or greater (2.0 and 3.9). In each of these families, two individuals from different generations carried the same recombinant chromosome, and all four individuals were without evidence of TSC after complete clinical exam and radiological study. Since non-penetrance in TSC is rare, we judged these individuals to provide additional positioning information and concentrated our search on the region between D9S2127 and DBH, a 900 kb interval.

Construction of a Cosmid Contig and Screening for Large Deletions

An important preliminary study involved the creation of a contig of cloned material for this region (Hornigold, et al., *Genomics* 41:385–389 (1997)). YACs proved to have limited value in this effort, and cosmids were used as the primary vehicle for construction of a contig, with filled-in of gaps using P1, PAC, and BAC clones. In a search for further positional information, 5 MluI restriction fragments covering the critical region were assayed in 265 unrelated patients with TSC using PFGE and hybridization to the probes shown in FIG. 1. No abnormalities suggestive of a genomic rearrangement were seen.

We also looked for deletions within the TSC1 region using a panel of 15 hybrid cell lines derived from patients from families with linkage to 9q34 and having a single chromosome 9 bearing the affected TSC1 allele. Analysis of these hybrid cell lines using 22 sets of primers derived from STSs and genes within the candidate region revealed no evidence of partial or complete deletion.

Gene Identification

From the cosmids, 142 exons were identified using exon-trapping methodology in the region between D9S1199 and D9S114. 13 novel genes from the region were identified in this manner (Table 1). Additional genes in the region were identified by cDNA selection methodology and use of cosmid DNA as probes for cDNA libraries. EST clones, mapped to this general genomic region by radiation hybrid mapping, were also mapped to specific cosmids. Several of the genes identified appeared to be good candidates based upon a probable or defined role in signal transduction pathways governing growth regulation. However, analysis of these genes did not reveal any evidence of mutation in patients with TSC.

A transcriptional unit denoted B2 was identified by hybridization of a cosmid containing D9S1830 (FIG. 1) to an arrayed infant brain library. Serial screening of a human fetal brain cDNA library with initial isolates yielded a cDNA clone of size 4.5 kb, which was sequenced and found to contain no open reading frame (ORF). Northern analysis showed a transcript of size 8.6 kb in every tissue tested (see below). Database searches revealed this clone was the 3' portion of a recently identified 6.8 kb cDNA clone (KIAA 0243, GenBank #D87683) Nagase, et al., DNA Res. 3: 321–329 (1996)), of unknown function with an ORF of 2 kb. This larger clone was obtained and the entire 6.8 kb cDNA was used to screen DNA samples from 150 unrelated TSC patients by Southern analysis after digestion with TaqIPstI HindIII, and EcoRI. No aberrant hybridization patterns were observed.

Genomic Sequencing and Screening for TSC-Associated Mutations

In parallel, we initiated a strategy to sequence the entire contig covering the 900 kb critical region, arguing that additional candidate genes would be discovered by this approach, and that the genomic sequence information would facilitate analysis of exons for mutations. After 208 kb of the genomic sequence of the region had been obtained, we had discovered an additional 4 probable new genes, and partial or complete genomic sequence information was derived for 3 genes identified in previous studies.

Figure 2A:
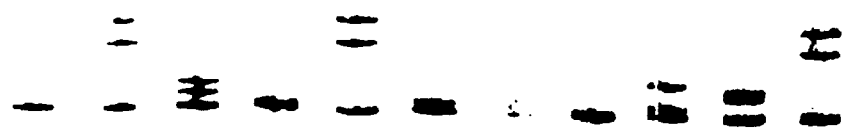
FIGS. 2A–D: Identification of Mutations in TSC1 Exon 15.

Putative exons predicted from the genomic sequence were PCR-amplified in a screening set of 60 DNA samples comprising an affected member of each of 20 unrelated TSC families showing linkage to 9q34 and 40 sporadic TSC cases. Heteroduplex analysis was employed to screen for mutations using weakly denaturing polyacrylamide gels. The 62nd exon screened was part of the previously identified B2 gene and demonstrated mobility shifts in 10 of the 60 patient samples (FIG. 2A). This exon was therefore subjected to detailed analysis.

Analysis of the Exon with Mobility Shifts

Figure 2B:
Figure 2C:
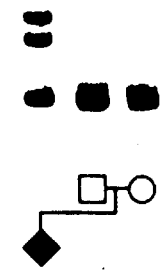
Figure 2D:
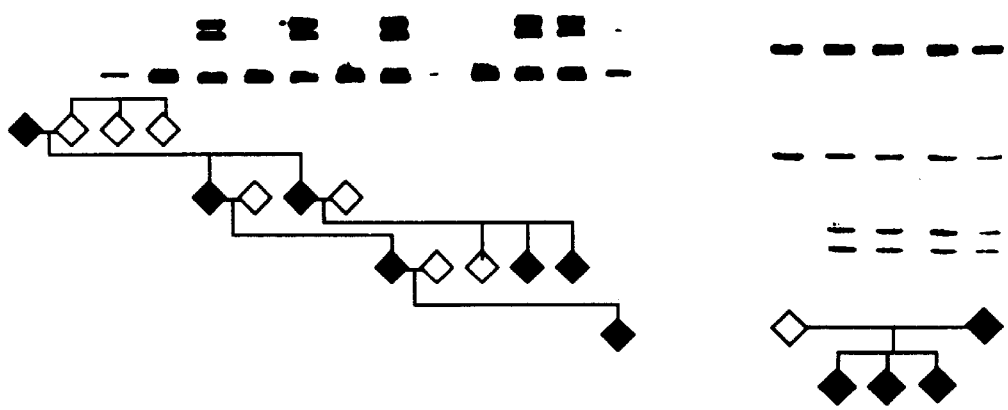

Sequencing of the amplified products associated with mobility shifts on heteroduplex analysis revealed 7 small frameshifting deletions (3 of which were identical), one nonsense mutation, one missense change, and one polymorphism which did not change the encoded amino acid (FIG. 2B, Table 2). Eight of the 9 mutations identified were from the 20 familial cases tested, with only one mutation seen among the 40 sporadic cases (FIG. 2C). Analysis of samples from other family members confirmed that each of the familial mutations segregated with TSC and that a frameshift mutation had occurred de novo in the sporadic case (FIG. 2D).

Haplotype analysis using markers flanking this exon (D9S2126, D9S1830, D9S1199) indicated that the recurrent mutation, 2105 delAAg, had occurred independently in 3 unrelated families, 2 polish and 1 American. These data showed that gene B2 was likely the TSC1 gene and further studies were undertaken to determine its structure and sequence.

The Complete Sequence and Structure of the TSC1 Gene

The 5' portion of the TSC1 gene was identified by 5' RACE. Some RACE clones had internal deletions when compared to the longest sequence obtained (FIG. 4). Oligonucleotide primers designed from these variably retained regions (bp 49–77 and bp 78–140) hybridized to distinct EcoRI fragments in cosmids telomeric to D9S1830, and comparison with other mapping studies indicated that they were located 5' to the remainder of the gene (bp 200–8600). This suggested that the regions represented variably spliced exons.

Figure 3:
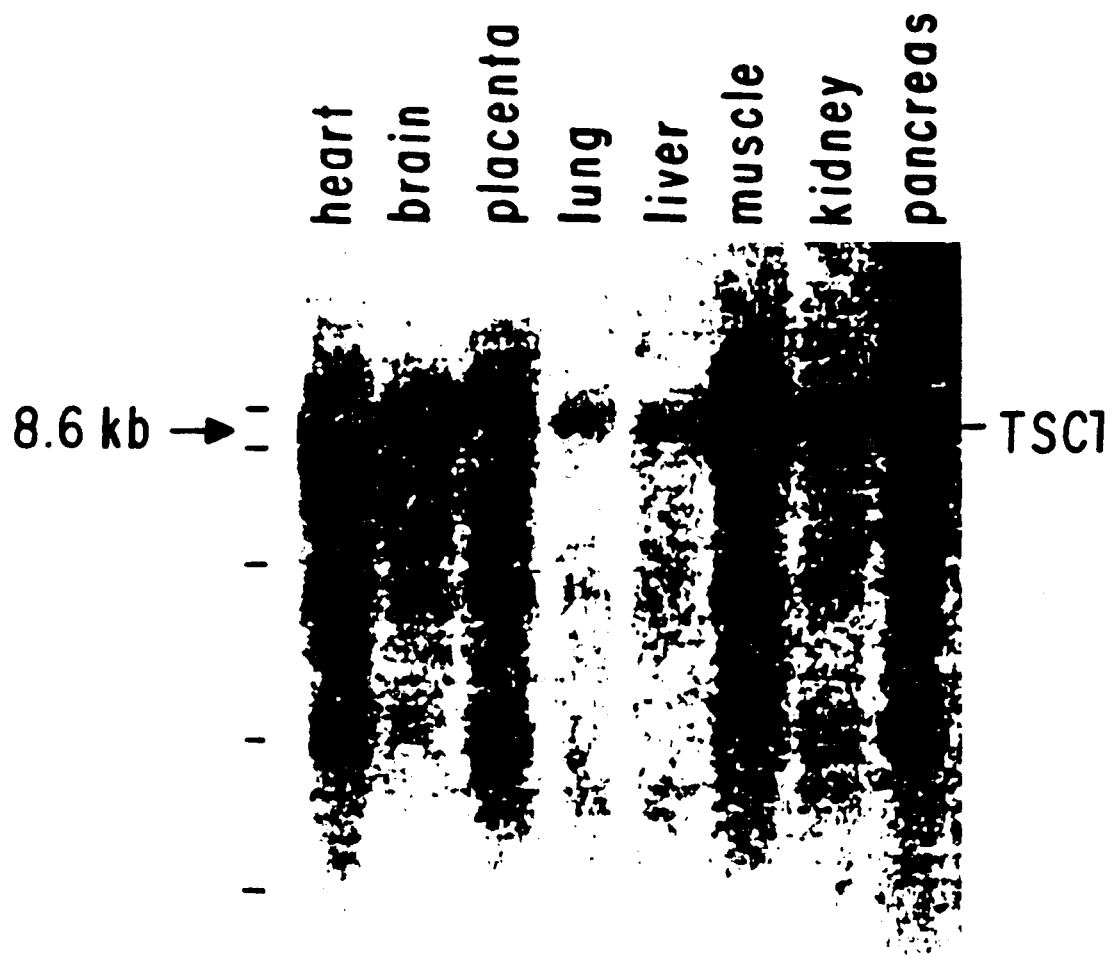
FIG. 3: Northern Blot Analysis of TSC1 Expression: Each lane shown in the figure contains 2 micrograms of poly A+ RNA from adult human organs. The probe used consisted of nucleotides 1100–2200 of the TSC1 gene. The lane labeled "muscle" is skeletal muscle.
Figure 5:
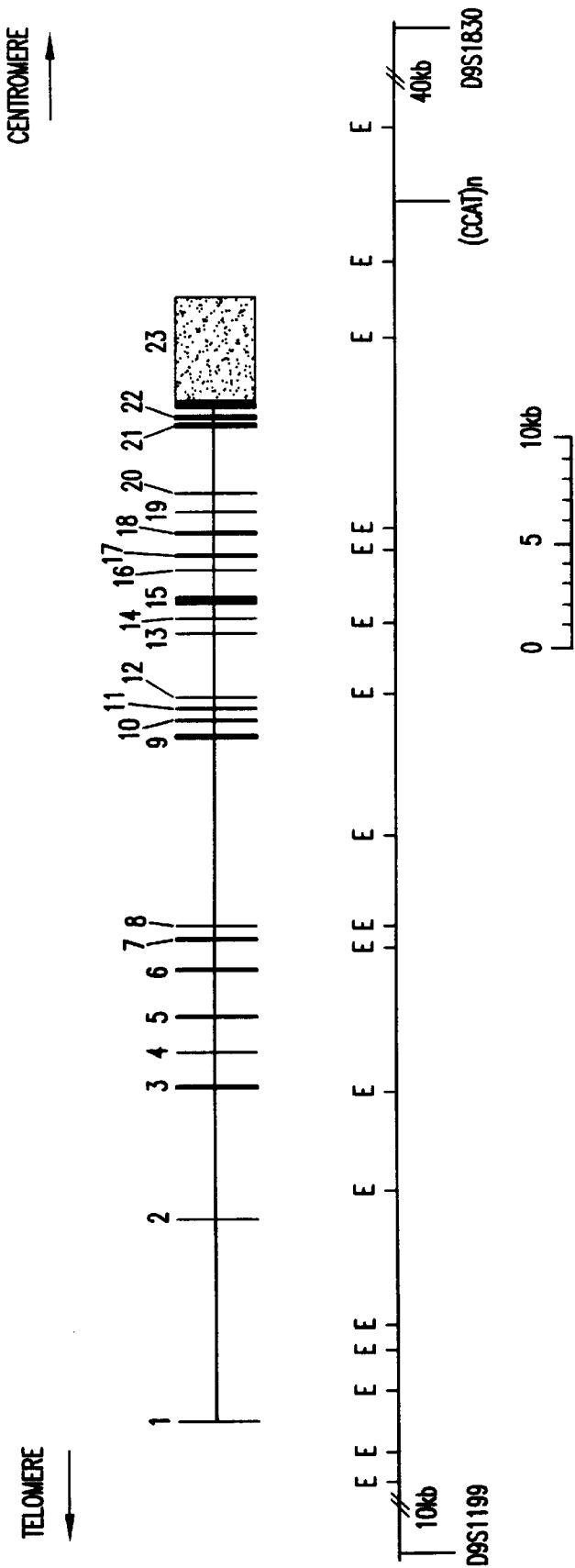
FIG. 5: Genomic Structure of TSC 1: The genomic structure of the TSC1 gene, including the positions of the 23 exons, is shown in the figure.

The open reading frame of the longest transcript begins at b162 with the first ATG codon at residue 222. Other methionine residues are found downstream in the same reading frame at positions 258 and 273. Translation may initiate at the first of these methionines, since it matches the Kozak consensus sequence for translation initiation (Kozak, Nucl. Acids Res. 15:(1987)). All three potential initiator methionines are 3' of the variable, presumably alternatively spliced, region and there is a 3' untranslated region of approximately 4.5 kb (see SEQ ID NO:1). Northern blot analysis with a coding region probe (bp 1100–2100) demonstrated a major 8.6 kb message that was widely expressed and that was particularly abundant in skeletal muscle (FIG. 3). The genomic structure of the TSC1 gene is shown in FIG. 5 and Table 3.

The predicted TSC1 protein, hamartin, is 1164 amino acid residues in length with a calculated mass of 130 kDa. The protein is generally hydrophilic and has a single potential transmembrane domain at amino acid residues 127–144 (Smith, et al., *Genome Res.* 6:454–462 (1996)). Database searches identified a possible homologue of TSC1 in the yeast *Schizosaccharomyces pombe* (GenBank #q09778), a hypothetical protein of Mw 103 kDa. There were no strong matches with known vertebrate proteins. Hamartin contains a potential coiled-coil region of 266 amino acids beginning at position 730 (Lupas, et al., *Science* 252:1162–1164 (1991)).

Other Mutations Found in TSC1

Because a high frequency of exon 15 mutations were identified in initial screens, we studied this exon in a larger sample of TSC patients. Mutations in exon 15 (559 bp, 16% coding region) were identified in 8 of 55 (15%) familial DNA samples, and in 15 of 607 (2.5%) of DNA samples from sporadic patients or unlinked families (Table 4). A screen for mutations in all coding exons in 20 familial cases and 152 sporadic patients yielded 8 mutations in each group (40% and 5%, respectively). In total, 19 mutations were found in coding exons other than exon 15. No mutations have been detected thus far in exons 3–6, 8, 11–14, 16 or 21–23. Of the 32 distinct mutations seen in 42 different patients/families, 5 were observed more than once. Thirty were predicted to be truncating, one was a missense mutation, and one was a splice site mutation.

Analysis of TSC Lesions Provides Evidence of the Tumor Suppressor Function of TSC1

Analysis of DNA from a renal cell carcinoma from a patient with germline mutation 2105delAAAG, revealed a somatic mutation, 1957delG, in the wild-type TSC1 allele. A giant cell astrocytoma from another patient with a germline 1942delGGinsTTGA mutation had retained the mutant allele but lost the wild-type allele. These results suggest that the wild-type TSC1 gene has the characteristics of a tumor suppressor.

TABLE 1

Genes Found in the TSC1 Critical Region

| Gene | Coding region | mRNA size | Expression | Function |
|---|---|---|---|---|
| A | 2 kb | 3 kb | ubiquitous | guanine nucleotide binding protein |
| VAV2 | 2.7 kb | 4 kb | ubiquitous | guanine nucleotide exchange factor |
| DMGdh | 3 kb | ND | liver | dimethlglycine dehydrogenase |
| B1 | >0.2 kb | ND | ND | unknown |
| E | >0.4 kb | 3 kb | brain, liver, kidney | unknown |
| kB2 | >2.3 kb | 4 kb | ubiquitous | thrombospondin homology |
| D | 0.7 kb | 2.6 kb | ubiquitous | unknown |
| C | >1.5 kb | 4.5 kb | liver | unknown |
| 6f | >0.6 kb | ND | ND | unknown |
| 3f | >0.6 kb | ND | ND | unknown |
| XPMC2H | 1.2 kb | 2.5 kb | ubiquitous | mitotic regulation (?) |
| RALGDS | 2.7 kb | 4.0 kb | ubiquitous | guanine nucleotide exchange factor |
| 9b9b | 1.5 kb | 2.0 kb | ubiquitous | unknown |
| A9 | | | | |
| B2 | 2 kb | 8.5 kb | ubiquitous | unknown |
| B11 | 4 kb | ND | ND | unknown |
| C10 | 0.6 kb | ND | ND | unknown |
| GR1 | 0.9 kb | ND | ND | adenylate kinase |
| GR2 | 1.3 kb | ND | ND | growth factor inhibitor |
| GR3 | >0.8 kb | ND | ND | unknown |
| GR4 | 2.3 kb | ND | ND | sugar transporter homology |

ND, not done.

TABLE 2

Mutations in TSC1 Found in Initial Screening

| UPN | Mutation | Number affected | Mutation Effect |
|---|---|---|---|
| MF24-1 | 1746C->T | 4 | truncation |
| MF12-1 | 1981A->G | 8 | K585R |
| MF6-1 | 2041delTT | 4 | truncation |
| MF3-1 | 2105delAAAG | 4 | truncation |
| Pol42-1 | 2105delAAAG | 2 | truncation |
| Pol74-1 | 2105delAAAG | 3 | truncation |
| MS91-1 | 2122delAC | 1 | truncation |
| MF11-1 | 2126delAG | 4 | truncation |
| MF14-1 | 2176delTG | 7 | truncation |

TABLE 3

Genomic Structure of the TSC1 Gene and Primers Used for PCR Analysis

| Exon | cDNA bp | Size | Genomic bp | Primers | SEQ ID NO |
|---|---|---|---|---|---|
| 9 | 959–1134 | 176 | 718–893 | ccagagacaaagttgcaaaacag; | 3 |
| | | | | ttgattacagtttgcatttcttgac | 4 |
| 10 | 1135–1250 | 116 | 1606–1721 | aaagcagaggagagagcagg; | 5 |
| | | | | cctaaaaccacacactaacccc | 6 |
| 11 | 1251–1362 | 112 | 2061–2172 | aaggcaggccaaaaccaac; | 7 |
| | | | | tgacttagcattcctttgccac | 8 |
| 12 | 1363–1484 | 122 | 2482–2603 | agtgagtcactgtgcctgg; | 9 |
| | | | | tgttctgcccttgtctctaag | 10 |
| 13 | 1485–1554 | 70 | 5804–5873 | ccaattagaagaggcaagc; | 11 |
| | | | | gcaacattttcgtcttgtg | 12 |
| 15 | 1660–2218 | 559 | 7035–7593 | gagagtgccccagtcccttac; | 13 |
| | | | | ccaggtggaataccgactgc | 14 |
| 16 | 2219–2262 | 44 | 8720–8763 | tggatttggagctaaagtaacaac; | 15 |

TABLE 3-continued

Genomic Structure of the TSC1 Gene and Primers Used for PCR Analysis

| Exon | cDNA bp | Size | Genomic bp | Primers | SEQ ID NO |
|---|---|---|---|---|---|
| 17 | 2263–2429 | 167 | 9357–9523 | cgtttttttcttggtaagatcg; tcatgctgacccaaaacaaaac; | 16 17 |
| 18 | 2430–2612 | 183 | 10387–10569 | aaaggcatttctgccaccc; actgactgcctccctcccc; | 18 19 |
| 19 | 2613–2723 | 111 | 11475–11585 | tcgcagtgtgtgttaaattgcc; acctgtctgaaggaagaatgttag; | 20 21 |
| 20 | 2724–2846 | 123 | 12337–12459 | cctcaaacttcatgtccacg; actgtctgggtctgaaacgc; | 22 23 |
| 21 | 2847–3034 | 188 | 15566–15753 | tttatgtcgtcggatttttcac; cacagtccttatgctggaattg; | 24 25 |
| 22 | 3035–3196 | 162 | 15831–15992 | tttttttcaggaagtagaaatgatg; cacagtccttatgctggaattg; | 26 25 |
| 23 | 3197–8600 | 5404 | 16422–21825 | tttttttcaggaagtagaaatgatg; cctcctgttctgtgccaac; tcaccagctccttttttcctc | 26 27 28 |

Note: Exons 21 and 22 were amplified as a single PCR product.

TABLE 4

All Mutations Found in TSC1

| Exon | # Patients Screened- familial (F)/other (S) | Mutations | Patients |
|---|---|---|---|
| 7 | 20F/152S | 865delTT | 1S |
| 9 | 39F/230S | 966delA | 1S |
| | | 970T->G,L250X | 1F |
| | | 993G->T,E258X | 1F |
| | | 1112T->G,Y297X | 1F |
| 10 | 20F/152S | 1207delCT | 1S |
| 15 | 55F/607S | 1746C->T,R509X | 2S, 1F |
| | | 1750delCA | 1S |
| | | 1801delAG | 1F |
| | | 1892del23 | 1S |
| | | 1929delAG | 2S |
| | | 1942delGGinsTTGA | 1S |
| | | 1981A->G,K585R | 1F |
| | | 2009delT | 1S |
| | | 2041delTT | 1F |
| | | 2060delA | 1S |
| | | 2105delAAAG | 4F, 2S |
| | | 2122delAC | 1S |
| | | 2126delAG | 1F, 1S |
| | | 2176delTG | 1F |
| 17 | 45F/296S | 2295C->T,R692X | 1F |
| | | 2324duplGTTACTC | 1S |
| | | 2332delAT | 1S |
| | | 2395insA | 1S |
| 18 | 45F/296S | 2448C->T,Q743X | 1S |
| | | 2519del23bp | 1S |
| | | 2540delC | 1F |
| | | 2577C->T,R786X | 1F, 1S |
| | | 2583G->T,E788X | 1F |
| 19 | 39F/230S | 2691delAC | 1S |
| 20 | 39F/230S | 2724-1G->T | 1F |
| | | 2730insA | 1S |

[1]Families with linkage to the TSC1 region and negative linkage to the TSC2 region (F); others (S) include both sporadic cases, and those from families without linkage information. See methods for further details.

III. Discussion

The TSC1 gene has been identified using a conventional positional cloning approach supplemented with genomic sequencing. Employing a mutation screening strategy scanning all possible exons, an exon from a recently identified gene of unknown function was found to contain several mutations in TSC patient DNA samples. The full genomic sequence of the TSC1 gene is presented and distinct mutations in apparently unrelated patients/families have been identified.

Based upon the studies discussed herein, the mutational spectrum of the TSC1 locus mainly comprises small deletions, small insertions, and point mutations which, in the majority of cases, are likely to inactivate protein function. This restricted mutational spectrum may reflect an intrinsic tendency for these types of mutations to occur in this region of the genome, or, alternatively, the strong negative survival effect of more disruptive mutations such as large deletions. Negative effects from large deletions are certainly possible given the high gene density near the TSC1 locus.

The results support the hypothesis that TSC1 functions as a tumor suppressor gene. First, the majority of mutations seen thus far are inactivating. Second, in two TSC associated tumors, there was loss of the wild-type TSC1 allele through loss of heterogeneity (LOH) or intragenic somatic mutation. The paucity of LOH for the TSC1 region among patient lesions examines today (Carbonara, et al., Cancer 15:18–25 (1996); Sepp, et al.,J. Med. Genet. 33:962–964 (1996)) may reflect the same mutational spectrum seen in the germline of TSC patients with a high frequency of small mutations causing inactivation of the second allele and/or a greater frequency of TSC2 involvement in the populations under study.

The TSC1 gene encodes a 1164 amino acid protein, termed hamartin which is generally hydrophilic and which contains a putative coiled-coil domain which is a potential site of protein-protein interaction. The specific biochemical mechanism by which loss of hamartin expression leads to development of TSC lesions is unknown. It is likely that hamartin and tuberin, the product of the TSC2 gene, participate in the same pathway of cellular growth control, since the clinical features of TSC due to the two genes are so similar. The sequence homology of hamartin to a putative *S. pombe* protein suggests that these proteins may participate in an evolutionarily conserved pathway of eukaryotic growth regulation. The identification of TSC1 will enable further analysis of the functions of these proteins, which will be important in unraveling the molecular pathogenesis of TSC.

All references cited are fully incorporated by reference. Having now fully described the invention, it will be understood by those of skill in the art that the invention may be performed within a wide and equivalent range of conditions, parameters, and the like, without affecting the spirit or scope of the invention or any embodiment thereof.

What is claimed is:

1. An isolated polynucleotide which encodes a protein consisting essentially of the amino acid sequence of SEQ ID NO:2.

2. A vector for expressing hamartin comprising the polynucleotide of claim 1.

3. A host cell transformed with the vector of claim 2.

4. The polynucleotide of claim 1, wherein said polynucleotide has a sequence consisting essentially of nucleotides 222–3713 of SEQ ID NO:1.

5. A vector for expressing hamartin comprising the polynucleotide of claim 4.

6. A host cell transformed with the vector of claim 5.

* * * * *

SEQUENCE LISTING (1) GENERAL INFORMATION:

(iii) NUMBER OF SEQUENCES: 28

(2) INFORMATION FOR SEQ ID NO:1:

(i) SEQUENCE CHARACTERISTICS:
      (A) LENGTH: 8600 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:1:

```
GTGCTGTACG TCCAAGATGG CGGCGCCTGT AGGCTGGAGG GACTGTGAGG TAAACAGCTG      60
AGGGGGAGGA GACGGTGGTG ACCATGAAAG ACACCAGGTT GACAGCACTG GAAACTGAAG     120
TACCAGTTGT CGCTAGAACA GTTTGGTAGT GGCCCCAATG AAGAACCTTC AGAACCTGTA     180
GCACACGTCC TGGAGCCAGC ACAGCGCCTT CGAGCGAGAG AATGGCCCAA CAAGCAAATG     240
TCGGGGAGCT TCTTGCCATG CTGGACTCCC CCATGCTGGG TGTGCGGGAC GACGTGACAG     300
CTGTCTTTAA AGAGAACCTC AATTCTGACC GTGGCCCTAT GCTTGTAAAC ACCTTGGTGG     360
ATTATTACCT GGAAACCAGC TCTCAGCCGG CATTGCACAT CCTGACCACC TTGCAAGAGC     420
CACATGACAA GCACCTCTTG GACAGGATTA ACGAATATGT GGGCAAAGCC GCCACTCGTT     480
TATCCATCCT CTCGTTACTG GGTCATGTCA TAAGACTGCA GCCATCTTGG AAGCATAAGC     540
TCTCTCAAGC ACCTCTTTTG CCTTCTTTAC TAAAATGTCT CAAGATGGAC ACTGACGTCG     600
TTGTCCTCAC AACAGGCGTC TTGGTGTTGA TAACCATGCT ACCAATGATT CCACAGTCTG     660
GGAAACAGCA TCTTCTTGAT TTCTTTGACA TTTTTGGCCG TCTGTCATCA TGGTGCCTGA     720
AGAAACCAGG CCACGTGGCG GAAGTCTATC TCGTCCATCT CCATGCCAGT GTGTACGCAC     780
TCTTTCATCG CCTTTATGGA ATGTACCCTT GCAACTTCGT CTCCTTTTTG CGTTCTCATT     840
ACAGTATGAA AGAAAACCTG GAGACTTTTG AAGAAGTGGT CAAGCCAATG ATGGAGCATG     900
TGCGAATTCA TCCGGAATTA GTGACTGGAT CCAAGGACCA TGAACTGGAC CCTCGAAGGT     960
GGAAGAGATT AGAAACTCAT GATGTTGTGA TCGAGTGTGC CAAAATCTCT CTGGATCCCA    1020
CAGAAGCCTC ATATGAAGAT GGCTATTCTG TGTCTCACCA AATCTCAGCC CGCTTTCCTC    1080
ATCGTTCAGC CGATGTCACC ACCAGCCCTT ATGCTGACAC ACAGAATAGC TATGGGTGTG    1140
CTACTTCTAC CCCTTACTCC ACGTCTCGGC TGATGTTGTT AAATATGCCA GGGCAGCTAC    1200
CTCAGACTCT GAGTTCCCCA TCGACACGGC TGATAACTGA ACCACCACAA GCTACTCTTT    1260
GGAGCCCATC TATGGTTTGT GGTATGACCA CTCCTCCAAC TTCTCCTGGA AATGTCCCAC    1320
CTGATCTGTC ACACCCTTAC AGTAAAGTCT TTGGTACAAC TGCAGGTGGA AAAGGAACTC    1380
CTCTGGGAAC CCCAGCAACC TCTCCTCCTC CAGCCCCACT CTGTCATTCG GATGACTACG    1440
TGCACATTTC ACTCCCCCAG GCCACAGTCA CACCCCCCAG GAAGGAAGAG AGAATGGATT    1500
CTGCAAGACC ATGTCTACAC AGACAACACC ATCTTCTGAA TGACAGAGGA TCAGAAGAGC    1560
CACCTGGCAG CAAAGGTTCT GTCACTCTAA GTGATCTTCC AGGGTTTTTA GGTGATCTGG    1620
CCTCTGAAGA AGATAGTATT GAAAAGATA AAGAAGAAGC TGCAATATCT AGAGAACTTT    1680
```

-continued

```
CTGAGATCAC CACAGCAGAG GCAGAGCCTG TGGTTCCTCG AGGAGGCTTT GACTCTCCCT    1740

TTTACCGAGA CAGTCTCCCA GGTTCTCAGC GGAAGACCCA CTCGGCAGCC TCCAGTTCTC    1800

AGGGCGCCAG CGTGAACCCT GAGCCTTTAC ACTCCTCCCT GGACAAGCTT GGGCCTGACA    1860

CACCAAAGCA AGCCTTTACT CCCATAGACC TGCCCTGCGG CAGTGCTGAT GAAAGCCCTG    1920

CGGGAGACAG GGAATGCCAG ACTTCTTTGG AGACCAGTAT CTTCACTCCC AGTCCTTGTA    1980

AAATTCCACC TCCGACGAGA GTGGGCTTTG GAAGCGGGCA GCCTCCCCCG TATGATCATC    2040

TTTTTGAGGT GGCATTGCCA AAGACAGCCC ATCATTTTGT CATCAGGAAG ACTGAGGAGC    2100

TGTTAAAGAA AGCAAAAGGA AACACAGAGG AAGATGGTGT GCCCTCTACC TCCCCAATGG    2160

AAGTGCTGGA CAGACTGATA CAGCAGGGAG CAGACGCGCA CAGCAAGGAG CTGAACAAGT    2220

TGCCTTTACC CAGCAAGTCT GTCGACTGGA CCCACTTTGG AGGCTCTCCT CCTTCAGATG    2280

AGATCCGCAC CCTCCGAGAC CAGTTGCTTT TACTGCACAA CCAGTTACTC TATGAGCGTT    2340

TTAAGAGGCA GCAGCATGCC CTCCGGAACA GGCGGCTCCT CCGCAAGGTG ATCAAAGCAG    2400

CAGCTCTGGA GGAACATAAT GCTGCCATGA AAGATCAGTT GAAGTTACAA GAGAAGGACA    2460

TCCAGATGTG GAAGGTTAGT CTGCAGAAAG AACAAGCTAG ATACAATCAG CTCCAGGAGC    2520

AGCGTGACAC TATGGTAACC AAGCTCCACA GCCAGATCAG ACAGCTGCAG CATGACCGAG    2580

AGGAATTCTA CAACCAGAGC CAGGAATTAC AGACGAAGCT GGAGGACTGC AGGAACATGA    2640

TTGCGGAGCT GCGGATAGAA CTGAAGAAGG CCAACAACAA GGTGTGTCAC ACTGAGCTGC    2700

TGCTCAGTCA GGTTTCCCAA AAGCTCTCAA ACAGTGAGTC GGTCCAGCAG CAGATGGAGT    2760

TCTTGAACAG GCAGCTGTTG GTTCTTGGGG AGGTCAACGA GCTCTATTTG AACAACTGC    2820

AGAACAAGCA CTCAGATACC ACAAAGGAAG TAGAAATGAT GAAAGCCGCC TATCGGAAAG    2880

AGCTAGAAAA AAACAGAAGC CATGTTCTCC AGCAGACTCA GAGGCTTGAT ACCTCCCAAA    2940

AACGGATTTT GGAACTGGAA TCTCACCTGG CCAAGAAAGA CCACCTTCTT TTGGAACAGA    3000

AGAAATATCT AGAGGATGTC AAACTCCAGG CAAGAGGACA GCTGCAGGCC GCAGAGAGCA    3060

GGTATGAGGC TCAGAAAAGG ATAACCCAGG TGTTTGAATT GGAGATCTTA GATTTATATG    3120

GCAGGTTGGA GAAAGATGGC CTCCTGAAAA AACTTGAAGA AGAAAAAGCA GAAGCAGCTG    3180

AAGCAGCAGA AGAAAGGCTT GACTGTTGTA ATGACGGGTG CTCAGATTCC ATGGTAGGGC    3240

ACAATGAAGA GGCATCTGGC CACAACGGTG AGACCAAGAC CCCCAGGCCC AGCAGCGCCC    3300

GGGGCAGTAG TGGAAGCAGA GGTGGTGGAG GCAGCAGCAG CAGCAGCAGC GAGCTTTCTA    3360

CCCCAGAGAA ACCCCACAC CAGAGGGCAG GCCCATTCAG CAGTCGGTGG GAGACGACTA    3420

TGGGAGAAGC GTCTGCCAGC ATCCCCACCA CTGTGGGCTC ACTTCCCAGT TCAAAAAGCT    3480

TCCTGGGTAT GAAGGCTCGA GAGTTATTTC GTAATAAGAG CGAGAGCCAG TGTGATGAGG    3540

ACGGCATGAC CAGTAGCCTT TCTGAGAGCC TAAAGACAGA ACTGGGCAAA GACTTGGGTG    3600

TGGAAGCCAA GATTCCCCTG AACCTAGATG GCCCTCACCC GTCTCCCCCG ACCCCGGACA    3660

GTGTTGGACA GCTACATATC ATGGACTACA ATGAGACTCA TCATGAACAC AGCTAAGGAA    3720

TGATGGTCAA TCAGTGTTAA CTTGCATATT GTTGGCACAG AACAGGAGGT GTGAATGCAC    3780

GTTTCAAAGC TTTCCTGTTT CCAGGGTCTG AGTGCAAGTT CATGTGTGGA AATGGGACGG    3840

AGGTCCTTTG GACAGCTGAC TGAATGCAGA ACGGTTTTTG GATCTGGCAT TGAAATGCCT    3900

CTTGACCTTC CCCTCCACCC GCCCTAACCC CCTCTCATTT ACCTCGCAGT GTGTTCTAAT    3960

CCAAGGGCCA GTTGGTGTTC CTCAGTAGCT TTACTTTCTT CCTTCCCCCC CAAATGGTTG    4020
```

```
CGTCCTTTGA ACCTGTGCAA TATGAGGCCA AATTTAATCT TTGAGTCTAA CACACCACTT    4080

TCTGCTTTCC CGAAGTTCAG ATAACTGGGT TGGCTCTCAA TTAGACCAGG TAGTTTGTTG    4140

CATTGCAGGT AAGTCTGGTT TTGTCCCTTC CAGGAGGACA TAGCCTGCAA AGCTGGTTGT    4200

CTTTACATGA AAGCGTTTAC ATGAGACTTT CCGACTGCTT TTTTGATTCT GAAGTTCAGC    4260

ATCTAAAGCA GCAGGTCTAG AAGAACAACG GTTTATTCAT ACTTGCATTC TTTTGGCAGT    4320

TCTGATAAGC TTCCTAGAAA GTTCTGTGTA AACAGAAGCC TGTTTCAGAA ATCTGGAGCT    4380

GGCACTGTGG AGACCACACA CCCTTTGGGA AAGCTCTTGT CTCTTCTTCC CCCACTACCT    4440

CTTATTTATT TGGTGTTTGC TTGAATGCTG GTACTATTGT GACCACAGGC TGGTGTGTAG    4500

GTGGTAAAAC CTGTTCTCCA TAGGAGGGAA GGAGCAGTCA CTGGGAGAGG TTACCCGAGA    4560

AGCACTTGAG CATGAGGAAC TGCACCTTTA GGCCATCTCA GCTTGCTGGG CCTTTTGTTA    4620

AACCCTTCTG TCTACTGGCC TCCCTTTGTG TGCATACGCC TCTTGTTCAT GTCAGCTTAT    4680

ATGTGACACT GCAGCAGAAA GGCTCTGAAG GTCCAAAGAG TTTCTGCAAA GTGTATGTGA    4740

CCATCATTTC CCAGGCCATT AGGGTTGCCT CACTGTAGCA GGTTCTAGGC TACCAGAAGA    4800

GGGGCAGCTT TTTCATACCA ATTCCAACTT TCAGGGCTG ACTCTCCAGG GAGCTGATGT     4860

CATCACACTC TCCATGTTAG TAATGGCAGA GCAGTCTAAA CAGAGTCCGG GAGAATGCTG    4920

GCAAAGGCTG GCTGTGTATA CCCACTAGGC TGCCCCACGT GCTCCCGAGA GATGACACTA    4980

GTCAGAAAAG TGGCAGTGGC AGAGAATCCA AACTCAACAA GTGCTCCTGA AAGAAATGCT    5040

AGAAGCCTAA GAACTGTGGT CTGGTGTTCC AGCTGAGGCA GGGGGATTTG GTAGGAAGGA    5100

GCCAGTGAAC TTGGCTTTCC TGTTTCTATC TTTCATTAAA AAGAATAGAA GGATTCAGTC    5160

ATAAAGAGGT AAAAAACTGT CACGGTACGA AATCTTAGTG CCTACGGAGG CCTCGAGCAG    5220

AAAGAATGAA AGTCTTTTTT TTTTTTTTT TTTTTTAGCA TGGCAATAAA TATTCTAGCA     5280

TCCCTAACTA AAGGGGACTA GACAGTTAGA GACTCTGTCA CCCTAGCTAT ACCAGCAGAA    5340

AACCTGTTCA GGCAGGCTTT CTGGGTGTGA CTGATTCCCA GCCTGTGGCA GGGCGTGGTC    5400

CCAACTACTC AGCCTAGCAC AGGCTGGCAG TTGGTACTGA ATTGTCAGAT GTGGAGTATT    5460

AGTGACACCA CACATTTAAT TCAGCTTTGT CCAAAGGAAA GCTTAAAACC CAATACAGTC    5520

TAGTTTCCTG GTTCCGTTTT AGAAAAGGAA AACGTGAACA AACTTAGAAA GGGAAGGAAA    5580

TCCCATCAGT GAATCCTGAA ACTGGTTTTA AGTGCTTTCC TTCTCCTCAT GCCCAAGAGA    5640

TCTGTGCCAT AGAACAAGAT ACCAGGCACT TAAAGCCTTT TCCTGAATTG GAAAGGAAAA    5700

GAGGCCCAAG TGCAAAAGAA AAAACATTTT AGAAACGGAC AGCTTATAAA AATAAAGGGA    5760

AGAAAGGAGG CAGCATGGAG AGAGGCCTGT GCTAGAAGCT CCATGGACGT GTCTGCACAG    5820

GGTCCTCAGC TCATCCATGC GGCCTGGGTG TCCTTTTACT CAGCTTTATA ACAAATGTGG    5880

CTCCAAGCTC AGGTGCCTTT GAGTTCTAGG AGGCTGTGGG TTTTATTCAA CTACGGTTGG    5940

GAGAATGAGA CCTGGAGTCA TGTTGAAGGT GCCCAACCTA AAAATGTAGG CTTTCATGTT    6000

GCAAAGAACT CCAGAGTCAG TAGTTAGGTT TGGTTTGGTT TTGGACATGA TAAACCTGCC    6060

AAGAGTCAAC AGGTCACTTG ATCATGCTGC AGTGGGTAGT TCTAAGGATG GAAAGGTGAC    6120

AGTATTACTC TCGAGAGGCA ATTCAGTCCT GGGCAAAGGT ATTAGTACAA TAAGCGTTAA    6180

GGGCAGAGTC TACCTTGAAA CCAATTAAGC AGCTTGGTAT TCATAAATAT TGGGATTGGA    6240

TGGCCTCCAT CCAGAAATCA CTATGGGTGA GCATACCTGT CTCAGCTGTT TGGCCAATGT    6300

GCATAACCTA CTCGGATCCC CACCTGACAC TAACCAGAGT CAGCACAGGC CCCGAGGAGC    6360
```

```
CCGAAGTTCT CTGCTGTGCA GCATGGAATT CCTTTAAAAA GGTGCACTAC AGTTTTAGCG    6420

GGGAGGGGGA TAGGAAGACG CAGAGCAAAT GAGCTCCGGA GTCCCTGCAG GTGAATAAAC    6480

ACACAGATCT GCATCTGATA GAACTTTGAT GGATTTTCAA AAAGCCGTTG ACAAGGCTCT    6540

GCTATACAGT CTATAAAAAT TGTTATTATG GGATTGGAAG AAACACATGG TCATGAATAG    6600

AAAAAAAACA AACCCAAAGG TAGGAAGGTC AAGGTCATTT CTTAGATGGA GAAGTTGTGA    6660

AAGATGTCCT TGGAGATGAG TTTTAGGACC AGCATTACTA AGGCAGGTGG GCAGACAGTG    6720

ACCTCTCTAG GTGTGTCCAC AGAGTTTTTC AGGAGAGAAA ACTGCCTGAC CTTTGGGACT    6780

AAGCTGCGGA ATCTTCTTAC TAAGCTTGAA GAGTGGAGAG GCGAGAGGTG AGCTACTTTG    6840

TGAGCCAAAG CTTATGTGAC ATGGTTGGGG AAACAGTCCA AACTGTTCTG AGAAGGTGAA    6900

CTGTTACGAC CCAGGACAAT TAGAAAAATT CACCCACCAT GCCGCACATT ACTGGGTAAA    6960

AGCAGGGCAG CAGGGAACAA AACTCCAGAC TCTTGGGCCG TCCCCATTTG CAACAGCACA    7020

CATAGTTTCT GGTATATTTG TTGGGAAAGA TAAAACTCTA GCAGTTGTTG AGGGGAGGAT    7080

GTATAAAATG GTCATGGGGA TGAAAGGATC TCTGAGACCA CAGAGGCTCA GACTCACTGT    7140

TAAGAATAGA AAACTGGGTA TGCGTTTCAT GTAGCCAGCA GAACTGAAGT GTGCTGTGAC    7200

AAGCCAATGT GAATTTCTAC CAAATAGTAG AGCATACCAC TTGAAGAAGG AAAGAACCGA    7260

AGAGCAAACA AAAGTTCTGC GTAATGAGAC TCACCTTTTC TCGCTGAAAG CACTAAGAGG    7320

TGGGAGGAGG CCTGCACAGG CTGGAGGAGG GTTTGGGCAG AGCGAAGACC CGGCCAGGAC    7380

CTTGGTGAGA TGGAGTGCCG CCCACCTCCT GCGGATACTC TTGGAGAGTT GTTCCCCCAG    7440

GGGNCTCTGC CCCACCTGGA GAAGGAAGCT GCCTGGTGTG GAGTGACTCA AATCAGTATA    7500

CCTATCTGCT GCACCTTCAC TCTCCAGGGT ACATGCTTTA AAACCGACCC GCAACAAGTA    7560

TTGGAAAAAT GTATCCAGTC TGAAGATGTT TGTGTATCTG TTTACATCCA GAGTTCTGTG    7620

ACACATGCCC CCCAGATTGC TGCAAAGATC CCAAGGCATT GATTGCACTT GATTAAGCTT    7680

TTGTCTGTAG GTGAAAGAAC AAGTTTAGGT CGAGGACTGG CCCCTAGGCT GCTGCTGTGA    7740

CCCTTGTCCC ATGTGGCTTG TTTGCCTGTC CGGGACTCTT CGATGTGCCC AGGGGAGCGT    7800

GTTCCTGTCT CTTCCATGCC GTCCTGCAGT CCTTATCTGC TCGCCTGAGG GAAGAGTAGC    7860

TGTAGCTACA AGGGAAGCCT GCCTGGAAGA GCCGAGCACC TGTGCCCATG GCTTCTGGTC    7920

ATGAAACGAG TTAATGATGG CAGAGGAGCT TCCTCCCCAC TTCGCAGCGC CACATTATCC    7980

ATCCTCTGAG ATAAGTAGGC TGGTTTAACC ATTGGAATGG ACCTTTCAGT GGAAACCCTG    8040

AGAGTCTGAG AACCCCCAGA CCAACCCTTC CCTCCCTTTC CCCACCTCTT ACAGTGTTTG    8100

GACAGGAGGG TATGGTGCTG CTCTGTGTAG CAAGTACTTT GGCTTATGAA AGAGGCAGCC    8160

ACGCATTTTG CACTAGGAAG AATCAGTAAT CACTTTTCAG AAGACTTCTA TGGACCACAA    8220

ATATATTACG GAGGAACAGA TTTTGCTAAG ACATAATCTA GTTTTATAAC TCAATCATGA    8280

ATGAACCATG TGTGGCAAAC TTGCAGTTTA AAGGGGTCCC ATCAGTGAAA GAAACTGATT    8340

TTTTTTAACG GACTGCTTTT AGTTAAATTG AAGAAAGTCA GCTCTTGTCA AAAGGTCTAA    8400

ACTTTCCCGC CTCAATCCTA AAAGCATGTC AACAATCCAC ATCAGATGCC ATAAATATGA    8460

ACTGCAGGAT AAAATGGTAC AATCTTAGTG AATGGGAATT GGAATCAAAA GAGTTTGCTG    8520

TCCTTCTTAG AATGTTCTAA AATGTCAAGG CAGTTGCTTG TGTTTAACTG TGAACAAATA    8580

AAAATTTATT GTTTTGCACT                                               8600
```

(2) INFORMATION FOR SEQ ID NO:2:

(i) SEQUENCE CHARACTERISTICS:
        (A) LENGTH: 1164 amino acids
        (B) TYPE: amino acid
        (C) STRANDEDNESS: Not Relevant
        (D) TOPOLOGY: Not Relevant (ii) MOLECULE TYPE: protein (iii) HYPOTHETICAL: NO (iv) ANTI-SENSE: NO (xi) SEQUENCE DESCRIPTION: SEQ ID NO:2:

```
Met Ala Gln Gln Ala Asn Val Gly Glu Leu Leu Ala Met Leu Asp Ser
 1               5                  10                  15

Pro Met Leu Gly Val Arg Asp Asp Val Thr Ala Val Phe Lys Glu Asn
            20                  25                  30

Leu Asn Ser Asp Arg Gly Pro Met Leu Val Asn Thr Leu Val Asp Tyr
        35                  40                  45

Tyr Leu Glu Thr Ser Ser Gln Pro Ala Leu His Ile Leu Thr Thr Leu
 50                  55                  60

Gln Glu Pro His Asp Lys His Leu Leu Asp Arg Ile Asn Glu Tyr Val
65                  70                  75                  80

Gly Lys Ala Ala Thr Arg Leu Ser Ile Leu Ser Leu Leu Gly His Val
                85                  90                  95

Ile Arg Leu Gln Pro Ser Trp Lys His Lys Leu Ser Gln Ala Pro Leu
            100                 105                 110

Leu Pro Ser Leu Leu Lys Cys Leu Lys Met Asp Thr Asp Val Val Val
        115                 120                 125

Leu Thr Thr Gly Val Leu Val Leu Ile Thr Met Leu Pro Met Ile Pro
130                 135                 140

Gln Ser Gly Lys Gln His Leu Leu Asp Phe Phe Asp Ile Phe Gly Arg
145                 150                 155                 160

Leu Ser Ser Trp Cys Leu Lys Lys Pro Gly His Val Ala Glu Val Tyr
                165                 170                 175

Leu Val His Leu His Ala Ser Val Tyr Ala Leu Phe His Arg Leu Tyr
            180                 185                 190

Gly Met Tyr Pro Cys Asn Phe Val Ser Phe Leu Arg Ser His Tyr Ser
        195                 200                 205

Met Lys Glu Asn Leu Glu Thr Phe Glu Glu Val Val Lys Pro Met Met
210                 215                 220

Glu His Val Arg Ile His Pro Glu Leu Val Thr Gly Ser Lys Asp His
225                 230                 235                 240

Glu Leu Asp Pro Arg Arg Trp Lys Arg Leu Glu Thr His Asp Val Val
                245                 250                 255

Ile Glu Cys Ala Lys Ile Ser Leu Asp Pro Thr Glu Ala Ser Tyr Glu
            260                 265                 270

Asp Gly Tyr Ser Val Ser His Gln Ile Ser Ala Arg Phe Pro His Arg
        275                 280                 285

Ser Ala Asp Val Thr Thr Ser Pro Tyr Ala Asp Thr Gln Asn Ser Tyr
290                 295                 300

Gly Cys Ala Thr Ser Thr Pro Tyr Ser Thr Ser Arg Leu Met Leu Leu
305                 310                 315                 320
```

```
Asn Met Pro Gly Gln Leu Pro Gln Thr Leu Ser Ser Pro Ser Thr Arg
                325                 330                 335

Leu Ile Thr Glu Pro Pro Gln Ala Thr Leu Trp Ser Pro Ser Met Val
                340                 345                 350

Cys Gly Met Thr Thr Pro Pro Thr Ser Pro Gly Asn Val Pro Pro Asp
                355                 360                 365

Leu Ser His Pro Tyr Ser Lys Val Phe Gly Thr Thr Ala Gly Gly Lys
            370                 375                 380

Gly Thr Pro Leu Gly Thr Pro Ala Thr Ser Pro Pro Ala Pro Leu
385                 390                 395                 400

Cys His Ser Asp Asp Tyr Val His Ile Ser Leu Pro Gln Ala Thr Val
                405                 410                 415

Thr Pro Pro Arg Lys Glu Arg Met Asp Ser Ala Arg Pro Cys Leu
                420                 425                 430

His Arg Gln His His Leu Leu Asn Asp Arg Gly Ser Glu Glu Pro Pro
            435                 440                 445

Gly Ser Lys Gly Ser Val Thr Leu Ser Asp Leu Pro Gly Phe Leu Gly
            450                 455                 460

Asp Leu Ala Ser Glu Glu Asp Ser Ile Glu Lys Asp Lys Glu Glu Ala
465                 470                 475                 480

Ala Ile Ser Arg Glu Leu Ser Glu Ile Thr Thr Ala Glu Ala Glu Pro
                485                 490                 495

Val Val Pro Arg Gly Gly Phe Asp Ser Pro Phe Tyr Arg Asp Ser Leu
                500                 505                 510

Pro Gly Ser Gln Arg Lys Thr His Ser Ala Ala Ser Ser Ser Gln Gly
            515                 520                 525

Ala Ser Val Asn Pro Glu Pro Leu His Ser Ser Leu Asp Lys Leu Gly
            530                 535                 540

Pro Asp Thr Pro Lys Gln Ala Phe Thr Pro Ile Asp Leu Pro Cys Gly
545                 550                 555                 560

Ser Ala Asp Glu Ser Pro Ala Gly Asp Arg Glu Cys Gln Thr Ser Leu
                565                 570                 575

Glu Thr Ser Ile Phe Thr Pro Ser Pro Cys Lys Ile Pro Pro Pro Thr
            580                 585                 590

Arg Val Gly Phe Gly Ser Gly Gln Pro Pro Tyr Asp His Leu Phe
            595                 600                 605

Glu Val Ala Leu Pro Lys Thr Ala His His Phe Val Ile Arg Lys Thr
            610                 615                 620

Glu Glu Leu Leu Lys Lys Ala Lys Gly Asn Thr Glu Glu Asp Gly Val
625                 630                 635                 640

Pro Ser Thr Ser Pro Met Glu Val Leu Asp Arg Leu Ile Gln Gln Gly
                645                 650                 655

Ala Asp Ala His Ser Lys Glu Leu Asn Lys Leu Pro Leu Pro Ser Lys
            660                 665                 670

Ser Val Asp Trp Thr His Phe Gly Gly Ser Pro Pro Ser Asp Glu Ile
            675                 680                 685

Arg Thr Leu Arg Asp Gln Leu Leu Leu His Asn Gln Leu Leu Tyr
            690                 695                 700

Glu Arg Phe Lys Arg Gln Gln His Ala Leu Arg Asn Arg Arg Leu Leu
705                 710                 715                 720

Arg Lys Val Ile Lys Ala Ala Ala Leu Glu Glu His Asn Ala Ala Met
                725                 730                 735
```

-continued

```
Lys Asp Gln Leu Lys Leu Gln Glu Lys Asp Ile Gln Met Trp Lys Val
            740                 745                 750

Ser Leu Gln Lys Glu Gln Ala Arg Tyr Asn Gln Leu Gln Glu Gln Arg
            755                 760                 765

Asp Thr Met Val Thr Lys Leu His Ser Gln Ile Arg Gln Leu Gln His
            770                 775                 780

Asp Arg Glu Glu Phe Tyr Asn Gln Ser Gln Glu Leu Gln Thr Lys Leu
785                 790                 795                 800

Glu Asp Cys Arg Asn Met Ile Ala Glu Leu Arg Ile Glu Leu Lys Lys
            805                 810                 815

Ala Asn Asn Lys Val Cys His Thr Glu Leu Leu Ser Gln Val Ser
            820                 825                 830

Gln Lys Leu Ser Asn Ser Glu Ser Val Gln Gln Met Glu Phe Leu
            835                 840                 845

Asn Arg Gln Leu Leu Val Leu Gly Glu Val Asn Glu Leu Tyr Leu Glu
            850                 855                 860

Gln Leu Gln Asn Lys His Ser Asp Thr Thr Lys Glu Val Glu Met Met
865                 870                 875                 880

Lys Ala Ala Tyr Arg Lys Glu Leu Glu Lys Asn Arg Ser His Val Leu
            885                 890                 895

Gln Gln Thr Gln Arg Leu Asp Ser Gln Lys Arg Ile Leu Glu Leu
            900                 905                 910

Glu Ser His Leu Ala Lys Lys Asp His Leu Leu Leu Glu Gln Lys Lys
            915                 920                 925

Tyr Leu Glu Asp Val Lys Leu Gln Ala Arg Gly Gln Leu Gln Ala Ala
            930                 935                 940

Glu Ser Arg Tyr Glu Ala Gln Lys Arg Ile Thr Gln Val Phe Glu Leu
945                 950                 955                 960

Glu Ile Leu Asp Leu Tyr Gly Arg Leu Glu Lys Asp Gly Leu Leu Lys
            965                 970                 975

Lys Leu Glu Glu Glu Lys Ala Glu Ala Ala Glu Ala Ala Glu Glu Arg
            980                 985                 990

Leu Asp Cys Cys Asn Asp Gly Cys Ser Asp Ser Met Val Gly His Asn
            995                 1000                1005

Glu Glu Ala Ser Gly His Asn Gly Glu Thr Lys Thr Pro Arg Pro Ser
            1010                1015                1020

Ser Ala Arg Gly Ser Ser Gly Ser Arg Gly Gly Gly Ser Ser Ser
1025                1030                1035                1040

Ser Ser Ser Glu Leu Ser Thr Pro Glu Lys Pro Pro His Gln Arg Ala
            1045                1050                1055

Gly Pro Phe Ser Ser Arg Trp Glu Thr Thr Met Gly Glu Ala Ser Ala
            1060                1065                1070

Ser Ile Pro Thr Thr Val Gly Ser Leu Pro Ser Ser Lys Ser Phe Leu
            1075                1080                1085

Gly Met Lys Ala Arg Glu Leu Phe Arg Asn Lys Ser Glu Ser Gln Cys
            1090                1095                1100

Asp Glu Asp Gly Met Thr Ser Ser Leu Ser Glu Ser Leu Lys Thr Glu
1105                1110                1115                1120

Leu Gly Lys Asp Leu Gly Val Glu Ala Lys Ile Pro Leu Asn Leu Asp
            1125                1130                1135

Gly Pro His Pro Ser Pro Pro Thr Pro Asp Ser Val Gly Gln Leu His
            1140                1145                1150
```

Ile Met Asp Tyr Asn Glu Thr His His Glu His Ser
        1155                1160

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(iii) HYPOTHETICAL: NO (iv) ANTI-SENSE: NO (xi) SEQUENCE DESCRIPTION: SEQ ID NO:3:

CCAGAGACAA AGTTGCAAAA CAG                                              23

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(iii) HYPOTHETICAL: NO (iv) ANTI-SENSE: NO (xi) SEQUENCE DESCRIPTION: SEQ ID NO:4:

TTGATTACAG TTTGCATTTC TTGAC                                            25

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(iii) HYPOTHETICAL: NO (iv) ANTI-SENSE: NO (xi) SEQUENCE DESCRIPTION: SEQ ID NO:5:

AAAGCAGAGG AGAGAGCAGG                                                  20

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(iii) HYPOTHETICAL: NO (iv) ANTI-SENSE: NO (xi) SEQUENCE DESCRIPTION: SEQ ID NO:6:

CCTAAAACCA CACACTAACC CC                                                    22

(2) INFORMATION FOR SEQ ID NO:7:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(iii) HYPOTHETICAL: NO (iv) ANTI-SENSE: NO (xi) SEQUENCE DESCRIPTION: SEQ ID NO:7:

AAGGCAGGCC AAAACCAAC                                                        19

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(iii) HYPOTHETICAL: NO (iv) ANTI-SENSE: NO (xi) SEQUENCE DESCRIPTION: SEQ ID NO:8:

TGACTTAGCA TTCCTTTGCC AC                                                    22

(2) INFORMATION FOR SEQ ID NO:9:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(iii) HYPOTHETICAL: NO (iv) ANTI-SENSE: NO (xi) SEQUENCE DESCRIPTION: SEQ ID NO:9:

AGTGAGTCAC TGTGCCTGG                                                        19

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(iii) HYPOTHETICAL: NO (iv) ANTI-SENSE: NO (xi) SEQUENCE DESCRIPTION: SEQ ID NO:10:

TGTTCTGCCC TTGTCTCTAA G                                                21

(2) INFORMATION FOR SEQ ID NO:11:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(iii) HYPOTHETICAL: NO (iv) ANTI-SENSE: NO (xi) SEQUENCE DESCRIPTION: SEQ ID NO:11:

CCAATTAGAA GAGGCAAGC                                                   19

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(iii) HYPOTHETICAL: NO (iv) ANTI-SENSE: NO (xi) SEQUENCE DESCRIPTION: SEQ ID NO:12:

GCAACATTTT TCGTCTTGTG                                                  20

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(iii) HYPOTHETICAL: NO (iv) ANTI-SENSE: NO (xi) SEQUENCE DESCRIPTION: SEQ ID NO:13:

GAGAGTGCCC CAGTCCCTTA C                                                21

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(iii) HYPOTHETICAL: NO (iv) ANTI-SENSE: NO (xi) SEQUENCE DESCRIPTION: SEQ ID NO:14:

CCAGGTGGAA TACCGACTGC                                              20

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(iii) HYPOTHETICAL: NO (iv) ANTI-SENSE: NO (xi) SEQUENCE DESCRIPTION: SEQ ID NO:15:

TGGATTTGGA GCTAAAGTAA CAAC                                         24

(2) INFORMATION FOR SEQ ID NO:16:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(iii) HYPOTHETICAL: NO (iv) ANTI-SENSE: NO (xi) SEQUENCE DESCRIPTION: SEQ ID NO:16:

CGTTTTTTTC TTGGTAAGAT CG                                           22

(2) INFORMATION FOR SEQ ID NO:17:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(iii) HYPOTHETICAL: NO (iv) ANTI-SENSE: NO (xi) SEQUENCE DESCRIPTION: SEQ ID NO:17:

TCATGCTGAC CCAAAACAAA AC                                           22

(2) INFORMATION FOR SEQ ID NO:18:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(iii) HYPOTHETICAL: NO (iv) ANTI-SENSE: NO (xi) SEQUENCE DESCRIPTION: SEQ ID NO:18:

AAAGGCATTT CTGCCACCC                                                            19

(2) INFORMATION FOR SEQ ID NO:19:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PCR primer"

(iii) HYPOTHETICAL: NO (iv) ANTI-SENSE: NO (xi) SEQUENCE DESCRIPTION: SEQ ID NO:19:

ACTGACTGCC TCCCTCCCC                                                            19

(2) INFORMATION FOR SEQ ID NO:20:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PCR primer"

(iii) HYPOTHETICAL: NO (iv) ANTI-SENSE: NO (xi) SEQUENCE DESCRIPTION: SEQ ID NO:20:

TCGCAGTGTG TGTTAAATTG CC                                                        22

(2) INFORMATION FOR SEQ ID NO:21:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PCR primer"

(iii) HYPOTHETICAL: NO (iv) ANTI-SENSE: NO (xi) SEQUENCE DESCRIPTION: SEQ ID NO:21:

ACCTGTCTGA AGGAAGAATG TTAG                                                      24

(2) INFORMATION FOR SEQ ID NO:22:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PCR primer"

(iii) HYPOTHETICAL: NO (iv) ANTI-SENSE: NO (xi) SEQUENCE DESCRIPTION: SEQ ID NO:22:

CCTCAAACTT CATGTCCACG                                                   20

(2) INFORMATION FOR SEQ ID NO:23:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PCR primer"

(iii) HYPOTHETICAL: NO (iv) ANTI-SENSE: NO (xi) SEQUENCE DESCRIPTION: SEQ ID NO:23:

ACTGTCTGGG TCTGAAACGC                                                   20

(2) INFORMATION FOR SEQ ID NO:24:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PCR primer"

(iii) HYPOTHETICAL: NO (iv) ANTI-SENSE: NO (xi) SEQUENCE DESCRIPTION: SEQ ID NO:24:

TTTATGTCGT CGGATTTTTC AC                                                22

(2) INFORMATION FOR SEQ ID NO:25:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PCR primer"

(iii) HYPOTHETICAL: NO (iv) ANTI-SENSE: NO (xi) SEQUENCE DESCRIPTION: SEQ ID NO:25:

CACAGTCCTT ATGCTGGAAT TG                                                22

(2) INFORMATION FOR SEQ ID NO:26:

(i) SEQUENCE CHARACTERISTICS:
            (A) LENGTH: 25 base pairs
            (B) TYPE: nucleic acid -continued

```
            (C) STRANDEDNESS: single
            (D) TOPOLOGY: linear (ii) MOLECULE TYPE: other nucleic acid
            (A) DESCRIPTION: /desc = "PCR primer"

(iii) HYPOTHETICAL: NO (iv) ANTI-SENSE: NO (xi) SEQUENCE DESCRIPTION: SEQ ID NO:26:

TTTTTTTCAG GAAGTAGAAA TGATG                                              25

(2) INFORMATION FOR SEQ ID NO:27:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PCR primer"

(iii) HYPOTHETICAL: NO (iv) ANTI-SENSE: NO (xi) SEQUENCE DESCRIPTION: SEQ ID NO:27:

CCTCCTGTTC TGTGCCAAC                                                     19

(2) INFORMATION FOR SEQ ID NO:28:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PCR primer"

(iii) HYPOTHETICAL: NO (iv) ANTI-SENSE: NO (xi) SEQUENCE DESCRIPTION: SEQ ID NO:28:

TCACCAGCTC CTTTTTTCCT C                                                  21
```